(12) United States Patent
Smit et al.

(10) Patent No.: US 12,037,382 B2
(45) Date of Patent: Jul. 16, 2024

(54) INVERSE AGONISTIC ANTI-US28 ANTIBODIES

(71) Applicant: Stichting VU, Amsterdam (NL)

(72) Inventors: Martine Joyce Smit, Amstrerdan (NL); Raimond Heukers, Utrecht (NL); Timo Werner Marcella De Groof, Ghent (BE); Tian Shu Fan, Leiden (NL); Raymond Henry De Wit, Amsterdam (NL)

(73) Assignee: Stichting VU, Amsterdam (NL)

(*) Notice: Subject to any disclaimer, the term of this patent is extended or adjusted under 35 U.S.C. 154(b) by 1004 days.

(21) Appl. No.: 16/967,269

(22) PCT Filed: Feb. 5, 2019

(86) PCT No.: PCT/NL2019/050072
§ 371 (c)(1),
(2) Date: Aug. 4, 2020

(87) PCT Pub. No.: WO2019/151865
PCT Pub. Date: Aug. 8, 2019

(65) Prior Publication Data
US 2021/0032316 A1 Feb. 4, 2021

(30) Foreign Application Priority Data
Feb. 5, 2018 (EP) .................................. 18155119

(51) Int. Cl.
*A61K 47/68* (2017.01)
*A61K 41/00* (2020.01)
*C07K 16/08* (2006.01)
*C07K 16/18* (2006.01)
*G01N 33/574* (2006.01)

(52) U.S. Cl.
CPC ........ *C07K 16/085* (2013.01); *A61K 41/0057* (2013.01); *A61K 47/6839* (2017.08); *A61K 47/6865* (2017.08); *C07K 16/18* (2013.01); *G01N 33/57492* (2013.01); *C07K 2317/31* (2013.01); *C07K 2317/565* (2013.01); *C07K 2317/569* (2013.01); *C07K 2317/92* (2013.01); *G01N 2333/045* (2013.01)

(58) Field of Classification Search
None
See application file for complete search history.

(56) References Cited

U.S. PATENT DOCUMENTS

2022/0324947 A1* 10/2022 Smit ................... C07K 16/088

FOREIGN PATENT DOCUMENTS

WO    WO2022162192    *  1/2021

OTHER PUBLICATIONS

Lunardi et al (Plos one 2007, v.2.*
Lerner Nature 1982; 299:592-596.*
Lloyd et al., 2009, Protein Engineering, v.22, pp. 159-168.*
Edwards et al., JMB 2003, v.334,pp. 103-118.*
Heukers et al, "The constitutive activity of the virally encoded chemokine receptor US28 accelerates glioblastoma growth",Oncogene, London, (Apr. 30, 2018), doi:10.1038/s41388-018-0255-7, ISSN 0950-9232, [T] 1-15. XP055475965.
Dziurzynski et al., "Consensus on the role of human cytomegalovirus in glioblastoma", Neuro-Oncology, US, (Feb. 8, 2012), vol. 14, No. 3, doi:10.1093/neuonc/nor227, ISSN 1522-8517, pp. 246-255, [Y] 1-15 . XP055328241.
Steeland et al, "Nanobodies as therapeutics: big opportunities for small antibodies", Drug Discovery Today, Elsevier, Amsterdam, NL, (Apr. 11, 2016), vol. 21, No. 7, doi:10.1016/J.DRUDIS.2016. 04.003, ISSN 1359-6446, pp. 1076-1113, [Y] 1-15. XP029598209.
Burg et al, "Structural basis for chemokine recognition and activation of a viral G protein-coupled receptor", Science (Washington D C), (Mar. 6, 2015), vol. 347, No. 6226, pp. 1113-1117, [Y] 1-15. XP002781153.
Mokros et al, "Surface expression and endocytosis of the human cytomegalovirus-encoded chemokine receptor US28 is regulated by agonist-independent phosphorylation.", Journal of Biological Chemistry, (Nov. 22, 2002), vol. 277, No. 47, ISSN 0021-9258, pp. 45122-45128, [Y] 1-15. XP002781152.
Lunardi et al, "Endothelial Cells' Activation and Apoptosis Induced by a Subset of Antibodies against Human Cytomegalovirus: Relevance to the Pathogenesis of Atherosclerosis", PLOS One, (May 2007), vol. 2, No. 5, ISSN 1932-6203, [Y] 1-15 XP002781151.

* cited by examiner

*Primary Examiner* — Michail A Belyavskyi
(74) *Attorney, Agent, or Firm* — Banner & Witcoff, Ltd.

(57) ABSTRACT

The invention relates to a novel class of antagonistic and inverse agonistic anti-US28 antibodies, more specifically to single heavy chain variable domain antibodies (VHH) and variants and modifications thereof. The invention further relates to methods for producing these antibodies and to the use of the antibodies in methods for diagnostic and therapeutic purposes, especially for treatment of an individual suffering from a CMV-positive tumor such as glioblastoma.

22 Claims, 12 Drawing Sheets
Specification includes a Sequence Listing.

A

B

```
                        SEQUENCE LISTING

<160> NUMBER OF SEQ ID NOS: 23

<210> SEQ ID NO 1
<211> LENGTH: 5
<212> TYPE: PRT
<213> ORGANISM: Artificial Sequence
<220> FEATURE:
<223> OTHER INFORMATION: CDR1
<220> FEATURE:
<221> NAME/KEY: VARIANT
<222> LOCATION: (1)..(1)
<223> OTHER INFORMATION: May be Y

<400> SEQUENCE: 1

Phe Thr Gly Val Ala
1               5

<210> SEQ ID NO 2
<211> LENGTH: 9
<212> TYPE: PRT
<213> ORGANISM: Artificial Sequence
<220> FEATURE:
<223> OTHER INFORMATION: CDR2
<220> FEATURE:
<221> NAME/KEY: VARIANT
<222> LOCATION: (1)..(1)
<223> OTHER INFORMATION: May be T or S
<220> FEATURE:
<221> NAME/KEY: VARIANT
<222> LOCATION: (2)..(2)
<223> OTHER INFORMATION: May be T or A
<220> FEATURE:
<221> NAME/KEY: VARIANT
<222> LOCATION: (4)..(4)
<223> OTHER INFORMATION: May be N
<220> FEATURE:
<221> NAME/KEY: VARIANT
<222> LOCATION: (7)..(7)
<223> OTHER INFORMATION: May be G
<220> FEATURE:
<221> NAME/KEY: VARIANT
<222> LOCATION: (9)..(9)
<223> OTHER INFORMATION: May be K

<400> SEQUENCE: 2

Leu Ile Thr Gly Asp Gly Ala Thr Arg
1               5
```

```
<210> SEQ ID NO 3
<211> LENGTH: 5
<212> TYPE: PRT
<213> ORGANISM: Artificial Sequence
<220> FEATURE:
<223> OTHER INFORMATION: CDR3
<220> FEATURE:
<221> NAME/KEY: VARIANT
<222> LOCATION: (4)..(4)
<223> OTHER INFORMATION: May be R
<220> FEATURE:
<221> NAME/KEY: VARIANT
<222> LOCATION: (5)..(5)
<223> OTHER INFORMATION: May be F

<400> SEQUENCE: 3

Lys Thr Gly Glu Tyr
1               5

<210> SEQ ID NO 4
<211> LENGTH: 21
<212> TYPE: PRT
<213> ORGANISM: Artificial Sequence
<220> FEATURE:
<223> OTHER INFORMATION: N-terminal extracellular region of US28
<220> FEATURE:
<221> NAME/KEY: VARIANT
<222> LOCATION: (8)..(8)
<223> OTHER INFORMATION: May be T
<220> FEATURE:
<221> NAME/KEY: VARIANT
<222> LOCATION: (15)..(15)
<223> OTHER INFORMATION: May be E
<220> FEATURE:
<221> NAME/KEY: VARIANT
<222> LOCATION: (18)..(18)
<223> OTHER INFORMATION: May be E or L
<220> FEATURE:
<221> NAME/KEY: VARIANT
<222> LOCATION: (19)..(19)
<223> OTHER INFORMATION: May be D or G

<400> SEQUENCE: 4

Met Thr Pro Thr Thr Thr Thr Ala Glu Leu Thr Thr Glu Phe Asp Tyr
1               5                   10                  15

Asp Asp Ala Thr Pro
            20

<210> SEQ ID NO 5
<211> LENGTH: 5
<212> TYPE: PRT
<213> ORGANISM: Artificial Sequence
<220> FEATURE:
<223> OTHER INFORMATION: CDR1 VHH
<220> FEATURE:
<221> NAME/KEY: misc_feature
<222> LOCATION: (1)..(1)
<223> OTHER INFORMATION: Xaa can be any naturally occurring amino acid

<400> SEQUENCE: 5

Xaa Thr Gly Val Ala
1               5

<210> SEQ ID NO 6
<211> LENGTH: 9
<212> TYPE: PRT
<213> ORGANISM: Artificial Sequence
<220> FEATURE:
<223> OTHER INFORMATION: CDR2 VHH
<220> FEATURE:
```

```
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 6

Xaa Xaa Thr Xaa Asp Gly Xaa Thr Xaa
1               5

<210> SEQ ID NO 7
<211> LENGTH: 5
<212> TYPE: PRT
<213> ORGANISM: Artificial Sequence
<220> FEATURE:
<223> OTHER INFORMATION: CDR3 VHH
<220> FEATURE:
<221> NAME/KEY: misc_feature
<222> LOCATION: (4)..(5)
<223> OTHER INFORMATION: Xaa can be any naturally occurring amino acid

<400> SEQUENCE: 7

Lys Thr Gly Xaa Xaa
1               5

<210> SEQ ID NO 8
<211> LENGTH: 5
<212> TYPE: PRT
<213> ORGANISM: Artificial Sequence
<220> FEATURE:
<223> OTHER INFORMATION: CDR1 VHH

<400> SEQUENCE: 8

Phe Thr Gly Val Ala
1               5

<210> SEQ ID NO 9
<211> LENGTH: 9
<212> TYPE: PRT
<213> ORGANISM: Artificial Sequence
<220> FEATURE:
<223> OTHER INFORMATION: CDR2 VHH

<400> SEQUENCE: 9

Leu Ile Thr Gly Asp Gly Ala Thr Arg
1               5

<210> SEQ ID NO 10
<211> LENGTH: 5
<212> TYPE: PRT
<213> ORGANISM: Artificial Sequence
<220> FEATURE:
<223> OTHER INFORMATION: CDR3 VHH

<400> SEQUENCE: 10

Lys Thr Gly Glu Tyr
1               5

<210> SEQ ID NO 11
```

<211> LENGTH: 114
<212> TYPE: PRT
<213> ORGANISM: Artificial Sequence
<220> FEATURE:
<223> OTHER INFORMATION: VUN100

<400> SEQUENCE: 11

Glu Val Gln Leu Val Glu Ser Gly Gly Gly Leu Val Gln Pro Gly Gly
1               5                   10                  15

Ser Leu Arg Leu Ala Cys Ala Val Ser Gly Pro Gly Leu Ile Phe Lys
            20                  25                  30

Phe Thr Gly Val Ala Trp Tyr Arg Arg Gln Val Pro Gly Ala Lys Arg
        35                  40                  45

Gly Leu Val Ala Leu Ile Thr Gly Asp Gly Ala Thr Arg Tyr Gly Asp
    50                  55                  60

Ser Val Lys Gly Arg Phe Thr Val Ser Arg Asp Ile Ala Ala Lys Arg
65                  70                  75                  80

Val Tyr Leu Glu Met Asn Asp Leu Arg Ser Glu Asp Thr Ala Val Tyr
                85                  90                  95

Tyr Cys Lys Thr Gly Glu Tyr Trp Gly Gln Gly Thr Gln Val Thr Val
            100                 105                 110

Ser Ser

<210> SEQ ID NO 12
<211> LENGTH: 111
<212> TYPE: PRT
<213> ORGANISM: Artificial Sequence
<220> FEATURE:
<223> OTHER INFORMATION: US28-Nb1

<400> SEQUENCE: 12

Glu Val Gln Leu Val Glu Ser Gly Gly Gly Leu Val Gln Ala Gly Gly
1               5                   10                  15

Ser Leu Arg Leu Ser Cys Val Val Ser Gly Thr Ile Phe Ser Tyr Thr
            20                  25                  30

Gly Val Ala Trp Tyr Arg Gln Thr Ser Gly Lys Gln Arg Glu Trp Val
        35                  40                  45

Ala Thr Thr Thr Asn Asp Gly Gly Thr Lys Phe Ala Asp Ser Val Lys
    50                  55                  60

Gly Arg Phe Thr Ile Ser Arg Asp Asn Ala Lys Lys Thr Val Tyr Leu
65                  70                  75                  80

Gln Met Asn Asn Leu Asn Ala Glu Asp Thr Ala Val Tyr Tyr Cys Lys
                85                  90                  95

Thr Gly Arg Phe Trp Gly Arg Gly Thr Leu Val Thr Val Ser Ser
            100                 105                 110

<210> SEQ ID NO 13
<211> LENGTH: 111
<212> TYPE: PRT
<213> ORGANISM: Artificial Sequence
<220> FEATURE:
<223> OTHER INFORMATION: US28-Nb2

<400> SEQUENCE: 13

Glu Val Gln Leu Val Glu Ser Gly Gly Gly Leu Val Gln Ala Gly Gly
1               5                   10                  15

Ser Leu Arg Leu Ser Cys Val Val Ser Gly Thr Ile Phe Ser Tyr Thr
            20                  25                  30

Gly Val Ala Trp Tyr Arg Gln Thr Ser Gly Asn Gln Arg Glu Trp Val

```
                35                  40                  45

Ala Thr Ala Thr Asn Asp Gly Gly Thr Lys Phe Ala Asp Ser Met Lys
             50                  55                  60

Gly Arg Phe Thr Ile Ser Arg Asp Asn Ala Lys Lys Thr Val Tyr Leu
 65                  70                  75                  80

Gln Met Asn Asn Leu Asn Ala Glu Asp Ala Ala Val Tyr Tyr Cys Lys
                 85                  90                  95

Thr Gly Arg Phe Trp Gly Arg Gly Thr Leu Val Thr Val Ser Ser
            100                 105                 110

<210> SEQ ID NO 14
<211> LENGTH: 111
<212> TYPE: PRT
<213> ORGANISM: Artificial Sequence
<220> FEATURE:
<223> OTHER INFORMATION: US28-Nb3

<400> SEQUENCE: 14

Glu Val Gln Leu Val Glu Ser Gly Gly Gly Leu Val Gln Ala Gly Gly
 1               5                  10                  15

Ser Leu Arg Leu Ser Cys Val Val Ser Gly Thr Ile Phe Ser Tyr Thr
            20                  25                  30

Gly Val Ala Trp Tyr Arg Gln Thr Ser Gly Asn Gln Arg Glu Trp Val
        35                  40                  45

Ala Ser Ala Thr Asn Asp Gly Gly Thr Lys Phe Ala Asp Ser Val Lys
     50                  55                  60

Gly Arg Phe Thr Ile Ser Arg Asp Asn Ala Lys Lys Thr Val His Leu
 65                  70                  75                  80

Gln Met Asn Asn Leu Asn Ala Glu Asp Ala Ala Val Tyr Tyr Cys Lys
                 85                  90                  95

Thr Gly Arg Phe Trp Gly Arg Gly Thr Leu Val Thr Val Ser Ser
            100                 105                 110

<210> SEQ ID NO 15
<211> LENGTH: 111
<212> TYPE: PRT
<213> ORGANISM: Artificial Sequence
<220> FEATURE:
<223> OTHER INFORMATION: US28-Nb4

<400> SEQUENCE: 15

Glu Val Gln Leu Val Glu Ser Gly Gly Gly Leu Val Gln Ala Gly Gly
 1               5                  10                  15

Ser Leu Arg Leu Ser Cys Val Val Ser Gly Thr Ile Phe Ser Tyr Thr
            20                  25                  30

Gly Val Ala Trp Tyr Arg Gln Pro Ser Gly Lys Gln Arg Glu Trp Val
        35                  40                  45

Ala Ser Ala Thr Asn Asp Gly Gly Thr Lys Phe Ala Asp Ser Val Lys
     50                  55                  60

Gly Arg Phe Thr Ile Ser Arg Asp Asn Ala Lys Lys Thr Val Tyr Leu
 65                  70                  75                  80

Gln Met Asn Asn Leu Asp Ala Asp Asp Thr Ala Val Tyr Tyr Cys Lys
                 85                  90                  95

Thr Gly Arg Phe Trp Gly Arg Gly Thr Leu Val Thr Val Ser Ser
            100                 105                 110

<210> SEQ ID NO 16
<211> LENGTH: 114
```

```
<212> TYPE: PRT
<213> ORGANISM: Artificial Sequence
<220> FEATURE:
<223> OTHER INFORMATION: Consensus VHH
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (27)..(29)
<223> OTHER INFORMATION: Xaa can be any naturally occurring amino acid
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid
<220> FEATURE:
<221> NAME/KEY: misc_feature
<222> LOCATION: (46)..(47)
<223> OTHER INFORMATION: Xaa can be any naturally occurring amino acid
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (61)..(63)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (87)..(87)
```

```
<223> OTHER INFORMATION: Xaa can be any naturally occurring amino acid
<220> FEATURE:
<221> NAME/KEY: misc_feature
<222> LOCATION: (89)..(90)
<223> OTHER INFORMATION: Xaa can be any naturally occurring amino acid
<220> FEATURE:
<221> NAME/KEY: misc_feature
<222> LOCATION: (102)..(103)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (109)..(109)
<223> OTHER INFORMATION: Xaa can be any naturally occurring amino acid

<400> SEQUENCE: 16

Glu Val Gln Leu Val Glu Ser Gly Gly Gly Leu Val Gln Xaa Gly Gly
1               5                   10                  15

Ser Leu Arg Leu Xaa Cys Xaa Val Ser Gly Xaa Xaa Xaa Ile Phe Xaa
            20                  25                  30

Xaa Thr Gly Val Ala Trp Tyr Arg Xaa Gln Xaa Xaa Gly Xaa Xaa Arg
        35                  40                  45

Xaa Xaa Val Ala Xaa Xaa Thr Xaa Asp Gly Xaa Thr Xaa Xaa Xaa Asp
    50                  55                  60

Ser Val Lys Gly Arg Phe Thr Xaa Ser Arg Asp Xaa Ala Xaa Lys Xaa
65                  70                  75                  80

Val Tyr Leu Xaa Met Asn Xaa Leu Xaa Xaa Glu Asp Thr Ala Val Tyr
                85                  90                  95

Tyr Cys Lys Thr Gly Xaa Xaa Trp Gly Xaa Gly Thr Xaa Val Thr Val
            100                 105                 110

Ser Ser

<210> SEQ ID NO 17
<211> LENGTH: 32
<212> TYPE: PRT
<213> ORGANISM: Artificial Sequence
<220> FEATURE:
<223> OTHER INFORMATION: consensus FR1
<220> FEATURE:
<221> NAME/KEY: VARIANT
<222> LOCATION: (14)..(14)
<223> OTHER INFORMATION: can also be P
<220> FEATURE:
<221> NAME/KEY: VARIANT
<222> LOCATION: (21)..(21)
<223> OTHER INFORMATION: Can also be A
<220> FEATURE:
<221> NAME/KEY: VARIANT
<222> LOCATION: (23)..(23)
<223> OTHER INFORMATION: can also be A
<220> FEATURE:
<221> NAME/KEY: VARIANT
<222> LOCATION: (27)..(27)
<223> OTHER INFORMATION: can also be P
<220> FEATURE:
<221> NAME/KEY: VARIANT
<222> LOCATION: (28)..(28)
<223> OTHER INFORMATION: optionally present
<220> FEATURE:
<221> NAME/KEY: VARIANT
<222> LOCATION: (29)..(29)
<223> OTHER INFORMATION: optionally present
<220> FEATURE:
<221> NAME/KEY: VARIANT
<222> LOCATION: (32)..(32)
<223> OTHER INFORMATION: can also be K
```

-continued

<400> SEQUENCE: 17

Glu Val Gln Leu Val Glu Ser Gly Gly Gly Leu Val Gln Ala Gly Gly
1               5                   10                  15

Ser Leu Arg Leu Ser Cys Val Val Ser Gly Thr Gly Leu Ile Phe Ser
            20                  25                  30

<210> SEQ ID NO 18
<211> LENGTH: 15
<212> TYPE: PRT
<213> ORGANISM: Artificial Sequence
<220> FEATURE:
<223> OTHER INFORMATION: consensus VHH FR2
<220> FEATURE:
<221> NAME/KEY: VARIANT
<222> LOCATION: (4)..(4)
<223> OTHER INFORMATION: optionally present
<220> FEATURE:
<221> NAME/KEY: VARIANT
<222> LOCATION: (6)..(6)
<223> OTHER INFORMATION: can also be V
<220> FEATURE:
<221> NAME/KEY: VARIANT
<222> LOCATION: (7)..(7)
<223> OTHER INFORMATION: can also be P
<220> FEATURE:
<221> NAME/KEY: VARIANT
<222> LOCATION: (9)..(9)
<223> OTHER INFORMATION: can also be A
<220> FEATURE:
<221> NAME/KEY: VARIANT
<222> LOCATION: (10)..(10)
<223> OTHER INFORMATION: can also be K
<220> FEATURE:
<221> NAME/KEY: VARIANT
<222> LOCATION: (12)..(12)
<223> OTHER INFORMATION: can also be G
<220> FEATURE:
<221> NAME/KEY: VARIANT
<222> LOCATION: (14)..(14)
<223> OTHER INFORMATION: can also be L

<400> SEQUENCE: 18

Trp Tyr Arg Arg Gln Thr Ser Gly Lys Gln Arg Glu Trp Val Ala
1               5                   10                  15

<210> SEQ ID NO 19
<211> LENGTH: 37
<212> TYPE: PRT
<213> ORGANISM: Artificial Sequence
<220> FEATURE:
<223> OTHER INFORMATION: consensus VHH FR3
<220> FEATURE:
<221> NAME/KEY: VARIANT
<222> LOCATION: (1)..(1)
<223> OTHER INFORMATION: can also be Y
<220> FEATURE:
<221> NAME/KEY: VARIANT
<222> LOCATION: (2)..(2)
<223> OTHER INFORMATION: can also be G
<220> FEATURE:
<221> NAME/KEY: VARIANT
<222> LOCATION: (11)..(11)
<223> OTHER INFORMATION: can also be V
<220> FEATURE:
<221> NAME/KEY: VARIANT
<222> LOCATION: (15)..(15)
<223> OTHER INFORMATION: can also be I
<220> FEATURE:
<221> NAME/KEY: VARIANT
<222> LOCATION: (17)..(17)
<223> OTHER INFORMATION: can also be A
<220> FEATURE:
<221> NAME/KEY: VARIANT
<222> LOCATION: (19)..(19)

```
<223> OTHER INFORMATION: can also be R
<220> FEATURE:
<221> NAME/KEY: VARIANT
<222> LOCATION: (23)..(23)
<223> OTHER INFORMATION: can also be E
<220> FEATURE:
<221> NAME/KEY: VARIANT
<222> LOCATION: (26)..(26)
<223> OTHER INFORMATION: can also be D
<220> FEATURE:
<221> NAME/KEY: VARIANT
<222> LOCATION: (28)..(28)
<223> OTHER INFORMATION: can also be R
<220> FEATURE:
<221> NAME/KEY: VARIANT
<222> LOCATION: (29)..(29)
<223> OTHER INFORMATION: can also be S

<400> SEQUENCE: 19

Phe Ala Asp Ser Val Lys Gly Arg Phe Thr Ile Ser Arg Asp Asn Ala
1               5                   10                  15

Lys Lys Thr Val Tyr Leu Gln Met Asn Asn Leu Asn Ala Glu Asp Thr
            20                  25                  30

Ala Val Tyr Tyr Cys
        35

<210> SEQ ID NO 20
<211> LENGTH: 11
<212> TYPE: PRT
<213> ORGANISM: Artificial Sequence
<220> FEATURE:
<223> OTHER INFORMATION: consensus VHH FR4
<220> FEATURE:
<221> NAME/KEY: VARIANT
<222> LOCATION: (3)..(3)
<223> OTHER INFORMATION: can also be G
<220> FEATURE:
<221> NAME/KEY: VARIANT
<222> LOCATION: (6)..(6)
<223> OTHER INFORMATION: can also be Q

<400> SEQUENCE: 20

Trp Gly Arg Gly Thr Leu Val Thr Val Ser Ser
1               5                   10

<210> SEQ ID NO 21
<211> LENGTH: 22
<212> TYPE: PRT
<213> ORGANISM: Human cytomegalovirus

<400> SEQUENCE: 21

Met Thr Pro Thr Thr Thr Thr Ala Glu Leu Thr Thr Glu Phe Asp Tyr
1               5                   10                  15

Asp Asp Glu Ala Thr Pro
            20

<210> SEQ ID NO 22
<211> LENGTH: 22
<212> TYPE: PRT
<213> ORGANISM: Human cytomegalovirus
```

```
<400> SEQUENCE: 22

Met Thr Pro Thr Thr Thr Thr Ala Glu Leu Thr Thr Glu Phe Asp Tyr
1               5                   10                  15

Asp Glu Asp Ala Thr Pro
            20

<210> SEQ ID NO 23
<211> LENGTH: 22
<212> TYPE: PRT
<213> ORGANISM: Human cytomegalovirus

<400> SEQUENCE: 23

Met Thr Pro Thr Thr Thr Thr Glu Leu Thr Thr Glu Phe Glu Tyr
1               5                   10                  15

Asp Leu Gly Ala Thr Pro
            20
```

INVERSE AGONISTIC ANTI-US28 ANTIBODIES

RELATED APPLICATIONS

This application is a National Stage Application under 35 U.S.C. 371 of co-pending PCT application PCT/NL2019/050072 designating the United States and filed Feb. 5, 2019; which claims the benefit of EP application number 18155119.3 and filed Feb. 5, 2018 each of which are hereby incorporated by reference in their entireties.

TECHNICAL FIELD OF THE INVENTION

The present invention relates to the field of virology. More specifically, the invention relates to single heavy chain variable domain antibodies which bind to the extracellular side, including for example the N-terminus, of G protein-coupled receptor US28 of human cytomegalovirus (HCMV). These antibodies are useful in methods for the diagnosis and treatment of HCMV-positive tumors.

BACKGROUND

Glioblastoma (GBM) is the most common type of human brain cancer and is characterized by severe aggressiveness. The disease accounts for over 45% of all malignant primary brain tumors with an age-adjusted incidence rate of 3 cases per 100,000 person-years (Ostrom et al., 2015. Neuro Oncol 17 Suppl 4: iv1-iv62). Despite aggressive therapeutic intervention by chemo/radiotherapy and surgical resection (Bush et al., 2017. Neurosurg Rev 40: 1-14), the clinical outcome is extremely poor with a median survival of only 15 months and overall 5-year survival rate of less than 5% (Ostrom et al., 2015. Ibid.). Human cytomegalovirus (HCMV) is widely spread in the population and establishes life-long latency in immunocompetent individuals (Vischer et al., 2014. Nature Rev Drug Disc 13: 123-39; Sinclair and Reeves, 2013. Viruses 5: 2803-24). Upon immunodeficiency (e.g. AIDS patients, allograft recipients, tumor-associated inflammation), the virus can be reactivated and cause severe pathologies (Lollinga et al., 2017. Transplantation 101: 531-540). HCMV DNA and proteins have been detected in most GBM samples (50-90%) as well as in several other cancer types, with surrounding healthy tissues being HCMV negative (Cobbs et al., 2002. Canc Res 62: 3347-50; Bhattacharjee et al., 2012. J Virol 86: 6815-24). The restricted expression of HCMV mRNA and/or protein (Cobbs, 2014. Neuro Oncol 16: 1435-6) and use of different methodologies has hampered the detection of HCMV RNA or proteins in GBM tissues (Taha et al., 2016. British J Neurosurg 30: 307-12). Nevertheless, treatment of HCMV-positive xenograft tumors in mice models with antiviral compounds reduces tumor growth and HCMV-directed immunotherapy show promise to improve patient outcome (Baryawno et al., 2011. J Clin Invest 121: 4043-55; Stragliotto et al., 2013. Int J Cancer 133:1204-13; Hadaczek et al., 2013. Clin Cancer Res 19: 6473-83; Mitchell et al., 2015. Nature 519:366-9). Moreover, moderate to high-grade HCMV infection was associated with poor survival of GBM patients (Rahbar et al., 2012. Herpesviridae 3: 3), which was extended by long-term adjuvant therapy with the HCMV-inhibitor valganciclovir (Soderberg-Naucler et al., 2013. N Engl J Med 369: 985-6; Peng et al., 2016. Mol Clin Oncol 4: 154-8). While there is consensus on the potential oncomodulatory role of HCMV in GBM (Dziurzynski et al., 2012. Neuro Oncol 14: 246-55), the mechanism by which HCMV exerts these effects remain incompletely understood.

HCMV encodes four viral G protein-coupled receptors (viral GPCRs: US27, UL78, UL33 and US28). Of these, US28 is the best characterized and, shares homology to the human chemokine receptor family. US28 is located on the virion and is subsequently expressed in HCMV-infected cells during all stages (i.e. latent and active states) of the viral life cycle (Humby and O'Connor, 2016. J Virol 90: 2959-70). Detection of US28 DNA, RNA or protein in GBM tissues requires sensitive techniques and particular immune-histochemical epitope unmasking approaches (Cobbs, 2014. Ibid.). Under these conditions, US28 was detected in 53-65% of the 35 different GBM tissues tested (Soroceanu et al., 2011. Cancer Res 71: 6643-53). US28 displays oncomodulatory activity via constitutive and promiscuous G protein coupling and subsequent signalling towards a broad panel of transcription factors and cytokines (e.g. NF-κB, STAT3, IL-6, TCF/LEF and HIF-1) that are involved in cell proliferation, survival, migration, angiogenesis and inflammation (Soroceanu et al., 2011. Ibid; Maussang et al., 2009. Cancer Res 69: 2861-9; Slinger et al., 2010. Sci Signal. 3: ra58; Maussang et al., 2006. PNAS 103: 13068-73; O'Hayre et al., 2013. Nat Rev Cancer 13: 412-24; Streblow et al., 1999. Cell 99: 511-20; de Wit et al., 2016. Oncotarget 7: 67966-67985). Additionally, US28 binds and internalizes a broad spectrum of human chemokines (e.g. CCL2/5, CX3CL1), which might contribute to immune evasion of infected host cells (Vischer et al., 2014. Ibid.). US28 has also been shown to be oncogenic, leading to tumor development when expressed in mouse 3T3 cells (Maussang et al., 2006. Ibid.). Moreover, the detection of US28 in GBM samples, together with its constitutive activity and promiscuous oncomodulatory signaling, turn US28 into a potential novel target in GBM (Soroceanu et al., 2011. Ibid.; Maussang et al., 2009. Ibid.; Slinger et al., 2010. Ibid.; Maussang et al., 2006. Ibid.).

In recent years, the development of antibody-based biologicals to target chemokine receptors is on the rise (Mujic-Delic et al., 2014. Trends Pharmacol Sci 35: 247-5526). In particular, small antibody fragments derived from heavy chain-only antibodies, also referred to as variable domains of heavy chain-only antibodies (VHHs) or Nanobodies® have shown great potential as detection tools, crystallization-chaperones and/or therapeutics for several receptor classes, including GPCRs (Mujic-Delic et al., 2014. Ibid.; Burg et al., 2015. Science 347: 1113-7; Manglik et al., 2017. Ann Rev Pharmacol Toxicol 57: 19-37). Recently, VHHs were developed to successfully target and inhibit the human chemokine receptors CXCR2, CXCR4 or CXCR7 (Bradley et al., 2015. Mol Pharmacol 87: 251-62; Jahnichen et al., 2010: PNAS 107: 20565-70; Maussang et al., 2013. JBC 288: 29562-72). Bivalent VHHs were shown to display inverse agonistic activities against a constitutively active CXCR4 mutant and CXCR2 (Bradley et al., 2015. Ibid.; Jahnichen et al., 2010: Ibid.). Furthermore, an intracellular-surface binding VHH was generated to obtain high resolution (2.9 Å) crystal structures of the active conformation of US28 (Burg et al., 2015. Ibid.).

SUMMARY OF THE INVENTION

Single heavy chain variable domain antibodies (VHH) were generated that specifically detect US28 in GBM tissues and inhibit ligand-dependent and constitutive US28 activity, which consequently impaired US28-dependent GBM growth in vitro and in vivo in an orthotopic xenograft model.

The results suggest an important role for US28 signaling in modulating HCMV-associated GBM growth. The US28-specific antibodies provide important research and diagnostic tools, which may further substantiate a role for HCMV-encoded US28 in HCMV-associated GBM. Moreover, they have therapeutic potential to improve the clinical outcome for patients with this devastating disease.

The invention therefore provides a single heavy chain variable domain antibody against human cytomegalovirus protein US28, which antibody binds to the extracellular region of US28, including, for example, the N-terminal extracellular region of US28, preferably the N-terminal extracellular region of US28 and the third extracellular loop of US28. Said single heavy chain variable domain antibody preferably comprises complementarity-determining regions (CDR) with amino acid sequences F/YTGVA for CDR1; L/T/SI/T/ATG/NDGA/GTR/K for CDR2; and KTGE/RY/F for CDR3. Said single heavy chain variable domain antibody may comprise human or humanized frame work regions.

An antibody according to the invention may be fused to an immunoglobulin Fc region or functional part thereof, preferably a Fc region or functional part thereof from, or derived from, IgG1, IgG2, IgG3, IgG4. Said Fc region or functional part thereof preferably is a human or a humanized *lama* Fc, or functional part thereof.

The invention further provides a bi- or multivalent antibody comprising the single heavy chain variable domain antibody according to the invention.

The invention further provides a bi- or multi-specific antibody comprising a heavy chain variable domain antibody according to the invention. Said bi- or multi-specific antibody preferably comprises a single heavy chain variable domain antibody against a serum protein, preferably against albumin.

The invention further provides an antibody according to the invention which is coupled to a detectable label such as a fluorescent label, a luminescent label, a (radio)isotopic label, and/or a paramagnetic label.

The invention further provides an antibody according to the invention which is coupled to a cytotoxic drug.

The invention further provides a method for producing a single heavy chain variable domain antibody according to the invention, the method comprising expressing a nucleic acid encoding an antibody of the invention in a relevant cell and recovering the thus produced antibody from the cell. Said relevant cell preferably is a bacterial cell, or a yeast cell.

The invention further provides an use of the antibody according to the invention for diagnostic applications.

The invention further provides an antibody according to the invention for use as a medicament.

The invention further provides a pharmaceutical composition comprising an antibody according to the invention.

The invention further provides an antibody according to the invention for use in a method for treatment of an individual suffering from a CMV-positive tumor such as, for example, a colon tumor, breast tumor, ovarian tumor or glioblastoma.

Figure 6:
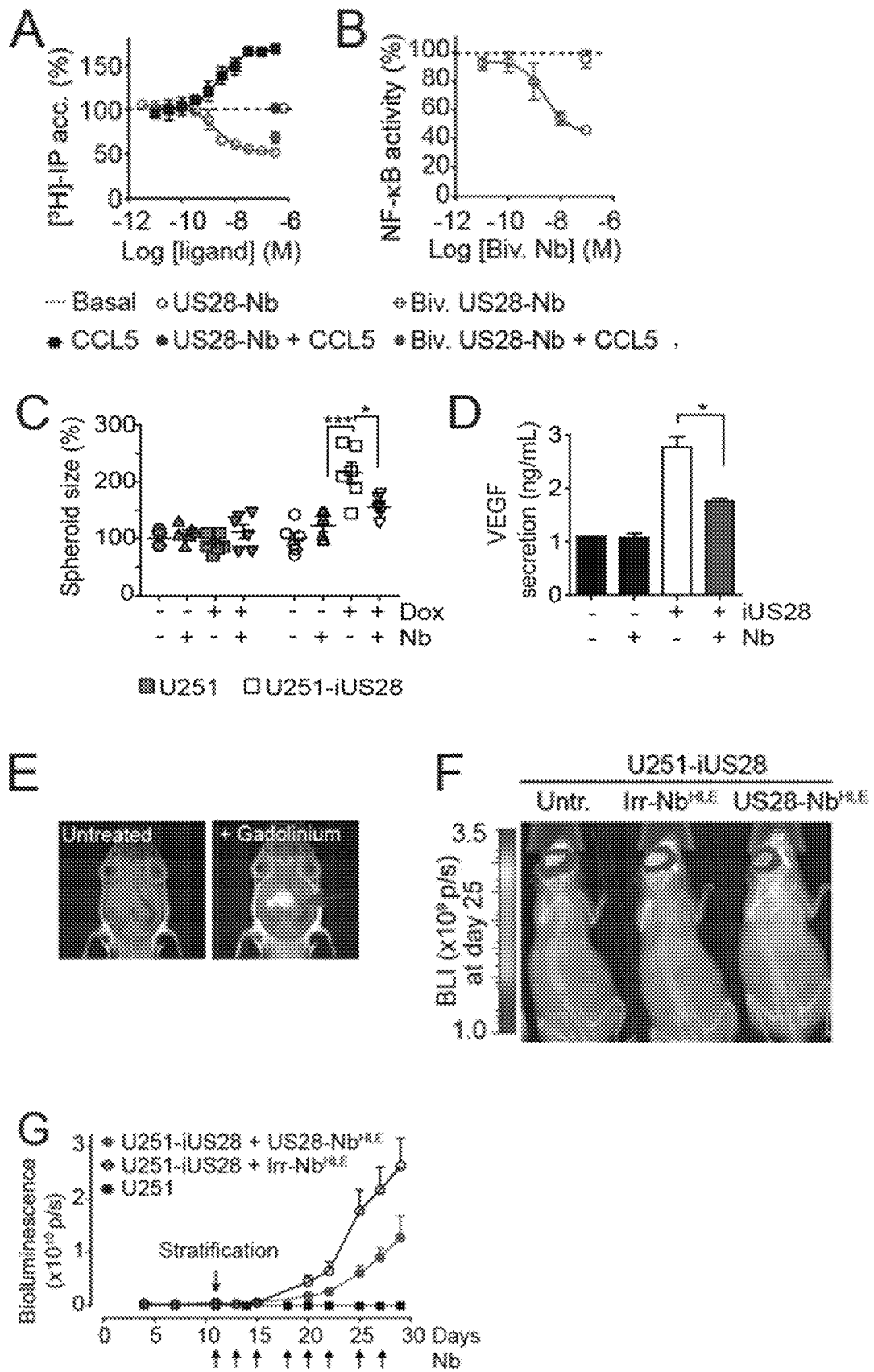

FIG. 6: Inhibition of US28-mediated GBM-growth by US28-specific VHHs. (A) US28-mediated accumulation of 3H-labeled inositol phosphates (IP) in US28-expressing HEK239T cells treated with either CCL5 alone (squares), monovalent US28 VHH either with (10-6.5 M VHH, filled circle) or without (10-6 M VHH, open circle) CCL5 (10-7.5 M) or bivalent US28-VHHs with (10-6.5 M, filled circle) or without (concentration range, open circles) CCL5 (10-7.5 M). IP levels were plotted in percentage of basal US28-mediated IP accumulation (dashed line). (B) US28-induced NF-κB reporter gene activation upon treatment with Biv. US28-Nb (solid line) or Mono US28-Nb (isolated point) in HEK239T cells, plotted in percentage of basal US28-mediated NF-κB activation (dashed line). (C) Inhibition of US28-mediated growth of U251-iUS28 spheroids by bivalent US28-Nbs (US28-Nb, 10-7 M), plotted in percentages as mean±SEM (n=6 spheroids per group). (D) Secretion of VEGF from U251-iUS28 spheroids upon treatment with bivalent US28-Nbs (10-7 M), as detected using ELISA. (E) T1 weighed MRI scan of a brain of one of the mice carrying an orthotopic doxycycline-induced U251-iUS28 tumor before (left) and after (right) intravenous administration of the contrast agent gadolinium. The impaired blood-brain barrier function in this tumor model is visualized by extravasation of gadolinium from the blood vasculature into the tumor. (F and G) Growth of orthotopic GBM tumors in mice upon treatment with half-life extended (HLE) bivalent US28-VHHs (US28-NbHLE, closed circles), or an irrelevant VHH (Irr.-NbHLE, open circles). VHH treatment (500 ug/injection, 3 times a week) was started upon tumor take and stratification of the mice (day 11). Pooled data of n=2 with 6 mice per group per experiment. ***P<0.001, *P<0.05 (unpaired t-test).

Figure 7:
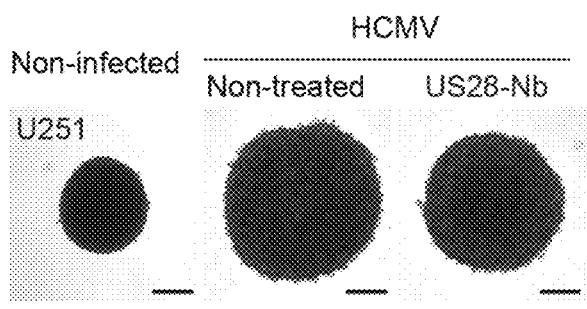
Figure 7:
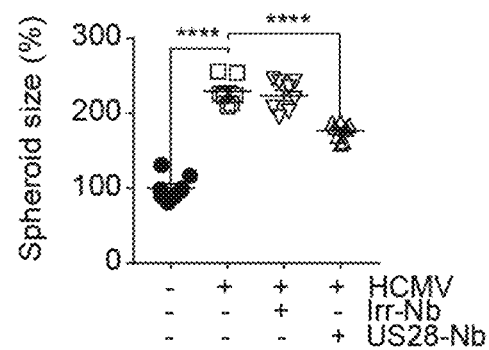
Figure 7:
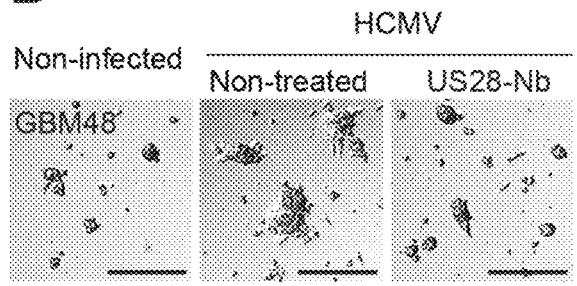
Figure 7:
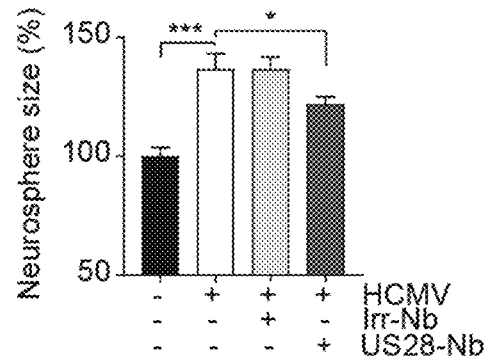

FIG. 7: VHHs impair HCMV-enhanced GBM spheroid growth. (A) Spheroid growth of U251 GBM cells infected with HCMV-Merlin upon treatment with Irr-Nb or US28-Nb (n=8 spheroids per group). (B) Neurosphere growth of HCMV-infected primary GBM48 cells upon treatment with Irr-Nb or US28-Nb (n=>150 neurospheres per group). All scale bars represent 250 µm. Individual spheroid- or neurosphere sizes were quantified and plotted in percentages with mean±SEM. **P<0.0001, *P<0.001, *P<0.05 (unpaired t-test).

Figure 8:
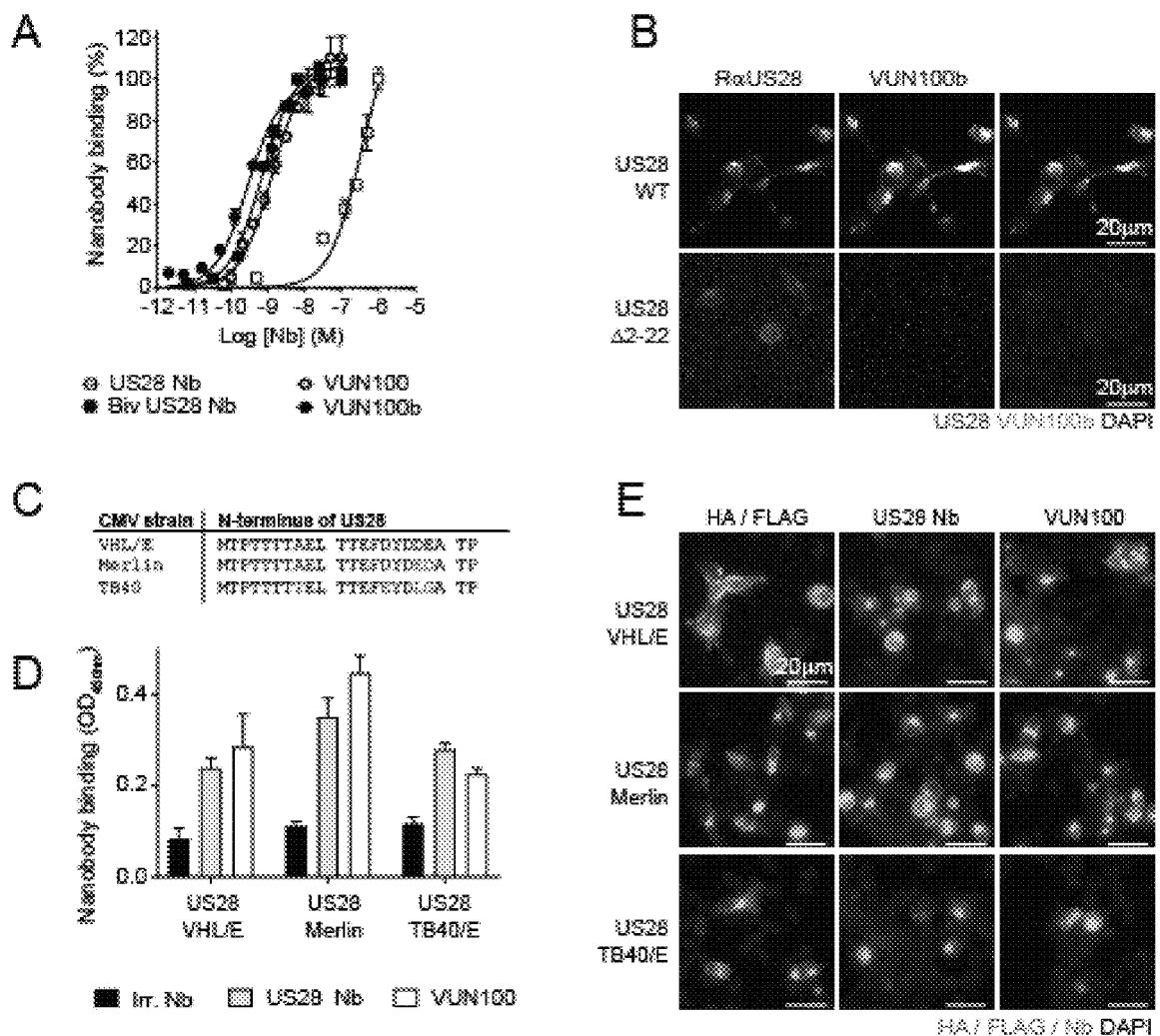
Figure 8:
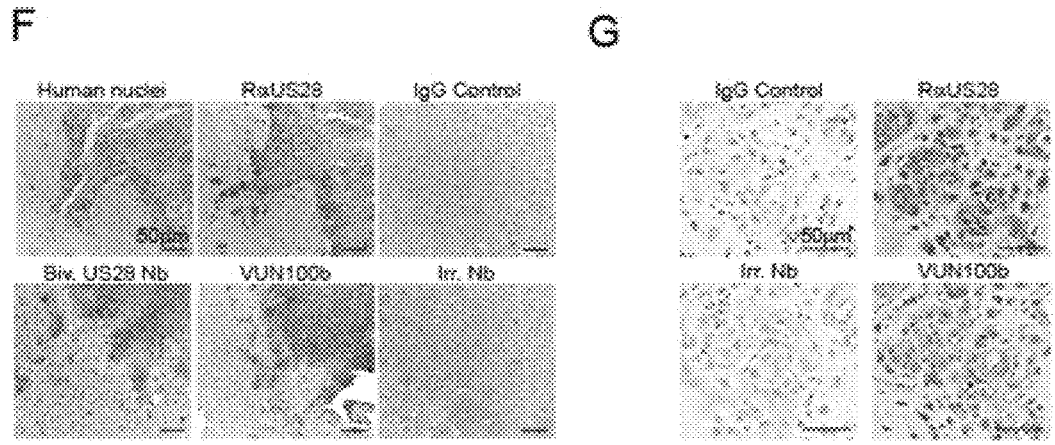

FIG. 8. US28-targeting VHH VUN100 binds the HCMV-encoded US28 with high affinity. A) Binding of monovalent and bivalent VHHs to US28-expressing membranes, as determined by ELISA. B) Immunofluorescence microscopy imaging showing binding of VHHs to HEK293T cells transfected with US28 wild type (WT, top), but not US28Δ2-22 (bottom). C) Alignment of the amino acid sequences of the N-terminal domain of US28 from different HCMV strains. Differences are indicated. D) Binding of VHHs to HEK293T cells transfected with US28 from different HCMV strains. VHHs were detected by ELISA as in A. Error bars represent SEM, where N=3. E) Immunofluorescent staining of the US28 VHH and VUN100 on HEK293T cells transfected as in D. F-G) Detection of US28 in paraffin-embedded sections from an orthotopic doxycycline-induced U251-iUS28 GBM model in the striatum of mice (F) or HCMV-infected GBM patient material (G). All VHHs were detected via their Myc tag. Nuclei were stained using DAPI or Hoechst staining.

Figure 9:
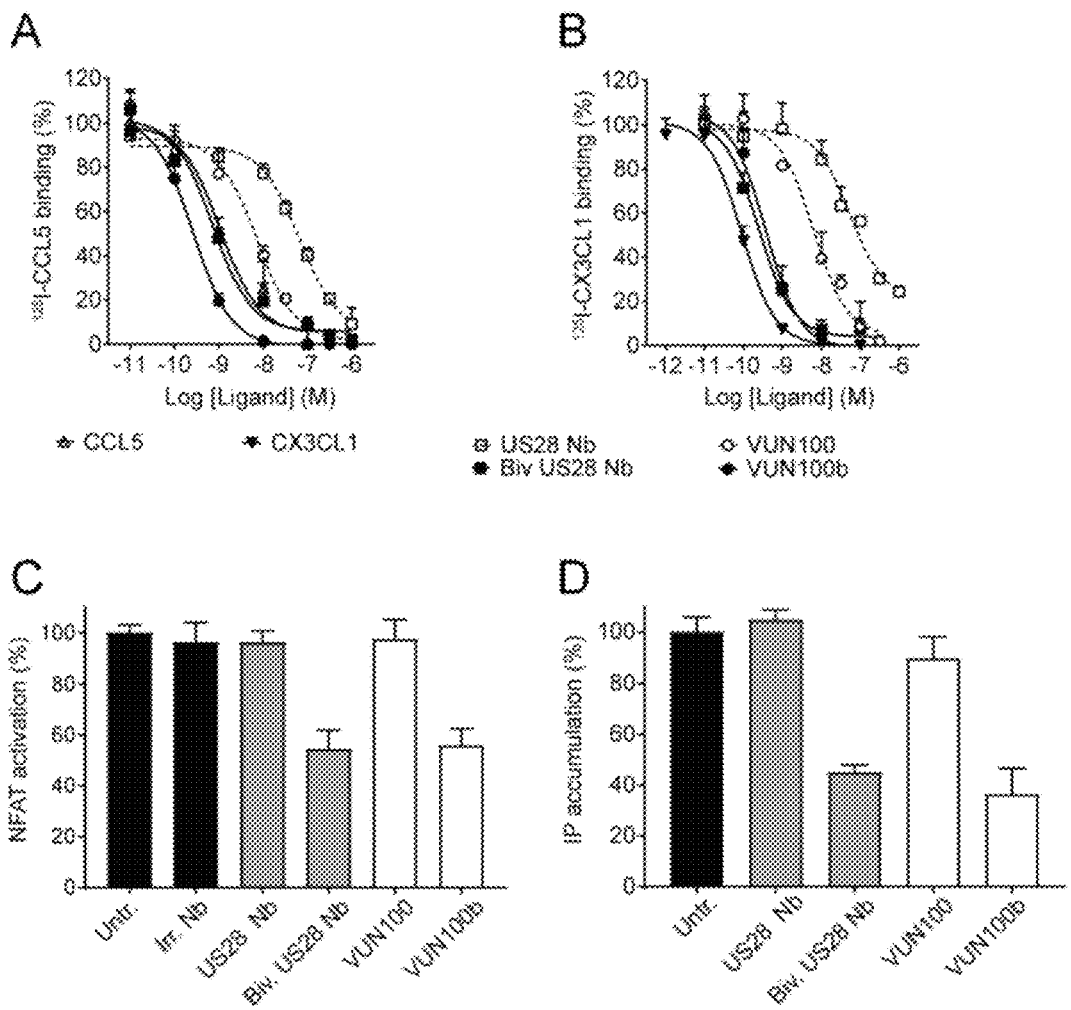

FIG. 9. US28-targeting VHHs compete for endogenous ligand binding and impair its constitutive activity. A-B) Binding competition of both monovalent and bivalent VHHs against $^{125}$I-CCL5 (A) and $^{125}$I-CX3CL1 (B) to US28. C-D) Effect of the VHHs on the constitutive activity of US28 measured by means of NFAT-reporter gene assay (C) and the accumulation of inositol phosphates (D).

Figure 10:
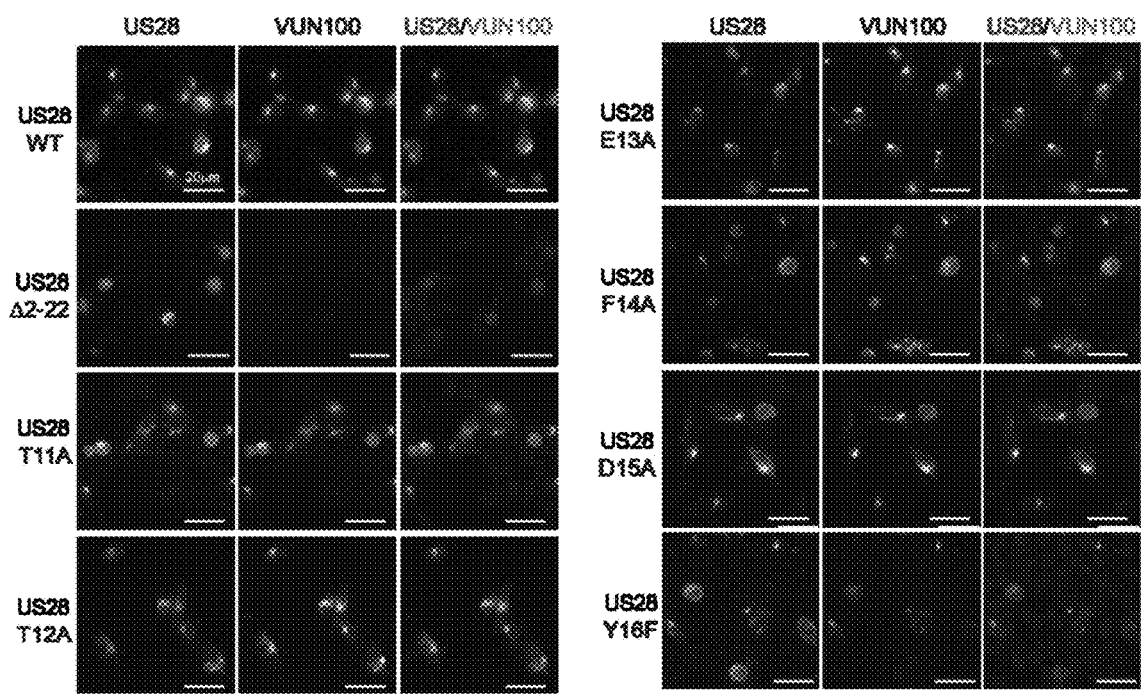
Figure 10:
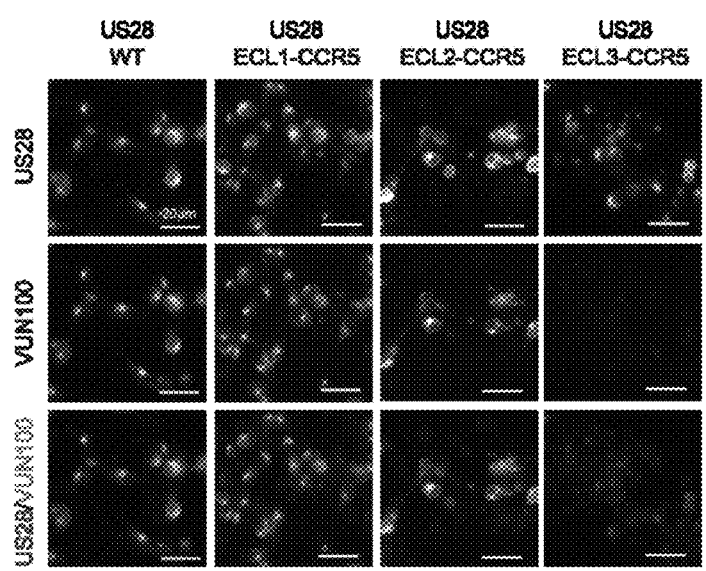

FIG. 10. Binding of VUN100 to US28 mutants. A) Immunofluorescence microscopy of binding of VUN100 to different US28 N-terminus mutants (A) and ECL chimaeras (B). The ECL1-3 of US28 have been swapped for the ECL1-3 of CCR5 to produce these US28 chimaeras (US28 ECL1-CCR5, US28 ECL2-CCR5 and US28 ECL3-CCR5).

Figure 11:
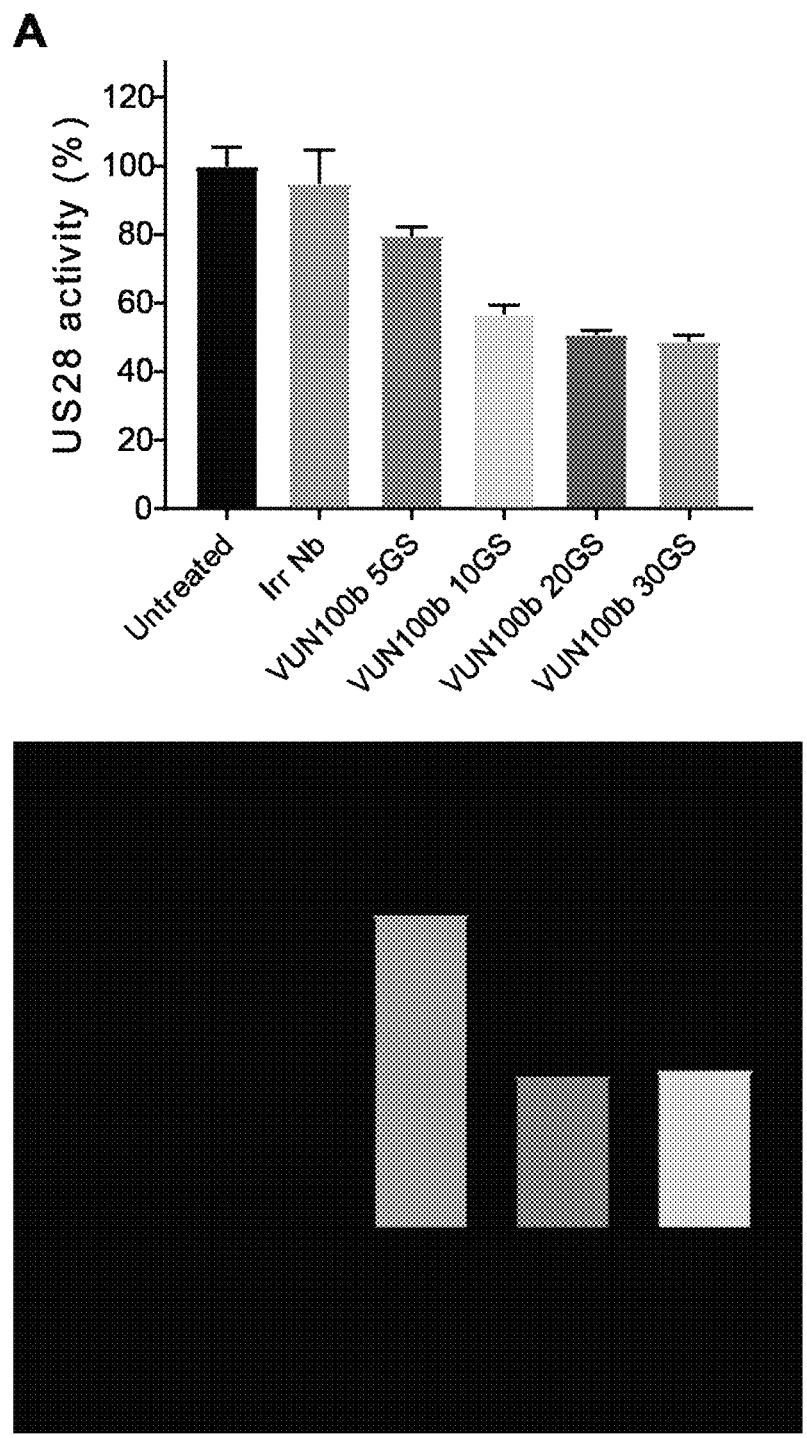

FIG. 11. Effect of US28 nanobodies on US28-mediated signaling. Bivalent VUN100 nanobodies with (A) flexible linkers of different lengths (VUN100 5-30GS) or (B) a rigid linker (VUN100-EAK) were tested on the US28-mediated inositol phosphate accumulation or NFAT activation. Irr Nb: irrelevant nanobody.

Figure 12:
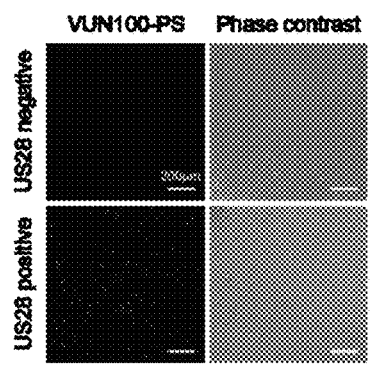
Figure 12:
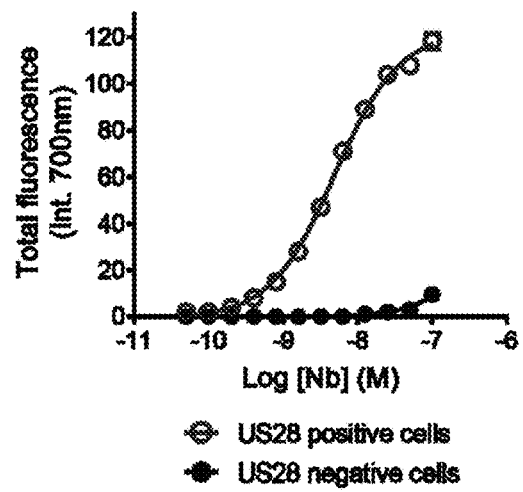
Figure 12:
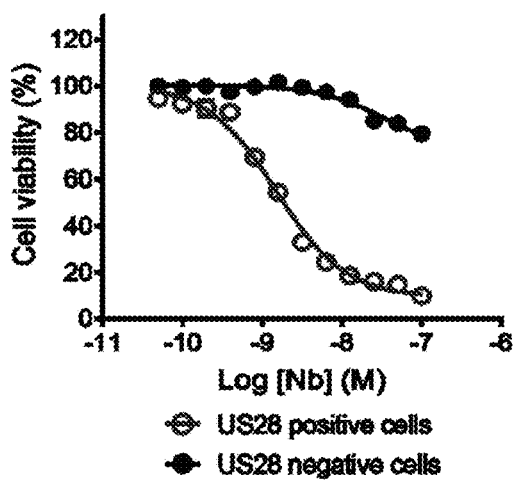
Figure 12:
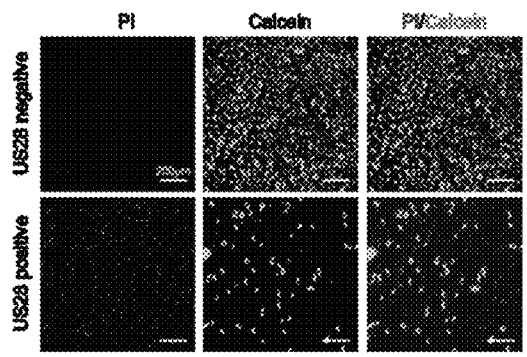
Figure 12:
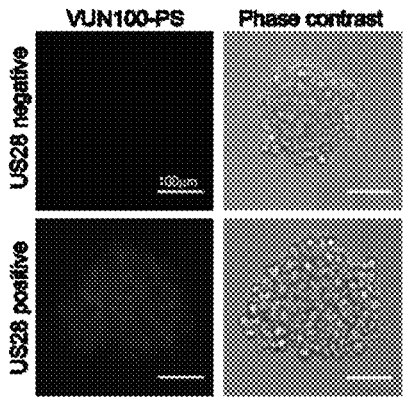
Figure 12:
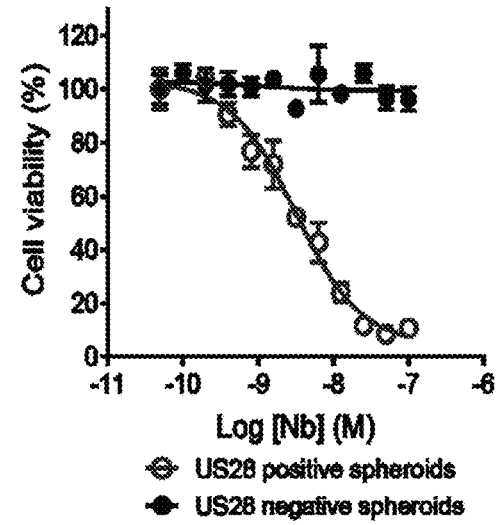

FIG. 12. VUN100-targeted PDT selectively kills US28 positive cells. A) VUN100-IRdye700DX (VUN100-PS) binds specifically to US28-positive glioblastoma cells (U28 positive) but not US28-negative glioblastoma cells (US28 negative). B) VUN100-PS was incubated for 1 h at 37° C. and specifically associated to US28 positive glioblastoma cells. C) VUN100-PS specifically induced phototoxicity in US28 positive glioblastoma cells upon treatment with near-infrared light. D) After PDT treatment, US28 positive and negative glioblastoma cells were stained with propidium iodide (PI) and Calcein to visualize dead and live cells. E) US28 positive and negative spheroids were incubated with VUN100-PS. Binding of VUN100-PS was visualized after washing of the spheroids. F) VUN100-PS specifically induced phototoxicity in US28 positive spheroids upon treatment with near-infrared light.

DETAILED DESCRIPTION OF THE INVENTION

Definitions

The term "antibody" as used herein, refers to an antigen binding protein comprising at least a heavy chain variable region (Vh) that binds to a target epitope. The term antibody includes monoclonal antibodies comprising immunoglobulin heavy and light chain molecules, single heavy chain variable domain antibodies, and variants and derivatives thereof, including chimeric variants of single heavy chain variable domain antibodies and multivalent and/or multispecific variants of single heavy chain variable domain antibodies.

The term "VHH", as used herein, refers to single heavy chain variable domain antibodies devoid of light chains. Preferably a VHH is an antibody of the type that can be found in Camelidae or cartilaginous fish which are naturally devoid of light chains or a synthetic antibody which can be constructed accordingly.

As described herein, the amino acid sequence and structure of a heavy chain variable domain, including a VHH, can be considered—without however being limited thereto—to be comprised of four framework regions or 'FR', which are referred to in the art and herein as 'Framework region 1' or 'FR'; as 'Framework region 2' or 'FR2'; as 'Framework region 3' or 'FR3'; and as 'Framework region 4' or 'FR4', respectively; which framework regions are interrupted by three complementary determining regions or 'CDR's', which are referred to in the art as 'Complementarity Determining Region 1' or 'CDR1'; as 'Complementarity Determining Region 2' or 'CDR2'; and as 'Complementarity Determining Region 3' or 'CDR3', respectively.

For the purpose of this patent application, amino acid residues 31-35 of VHH are defined as CDR1, amino acid residues 50-57 of VHH are defined as CDR2, and amino acid residues 97-100 of VHH are defined as CDR3, with the amino acid residue numbering according to according to Riechmann and Muyldermans, 1999. J Immunol Methods 23: 25-38, as is indicated in Table 1.

The total number of amino acid residues of a VHH is typically in the region of 110-120, is preferably 111-115, and is most preferably 113.

The term 'binding' as used herein in the context of binding between an antibody, preferably a VHH, and an epitope of US28 as a target, refers to the process of a non-covalent interaction between molecules. Preferably, said binding is specific. The terms 'specific' or 'specificity' or grammatical variations thereof refer to the number of different types of antigens or their epitopes to which a particular antibody such as a VHH can bind. The specificity of an antibody can be determined based on affinity. A specific antibody preferably has a binding affinity Kd for its specific epitope of less than $10^{-7}$ M, preferably less than $10^{-8}$ M.

The term affinity refers to the strength of a binding reaction between a binding domain of an antibody and an epitope. It is the sum of the attractive and repulsive forces operating between the binding domain and the epitope. The term affinity, as used herein, refers to the apparent binding affinity, which is determined as the equilibrium dissociation constant (Kd).

The term epitope or antigenic determinant refers to a part of an antigen that is recognized by an antibody. The term epitope includes linear epitopes and conformational epitopes, also referred to as continuous and discontinuous epitopes respectively. A conformational epitope is based on 3-D surface features and shape and/or tertiary structure of the antigen. A posttranslational modification, such as phosphorylation, glycosylation, methylation, acetylation and lipidation, may be relevant for an epitope for recognition by a specific antibody.

The term CMV refers to a virus of the genus Cytomegalovirus, which currently harbours eight species. Human cytomegalovirus (HCMV), also termed human herpesvirus 5 (HHV-5) is the type species.

The term US28 refers to a G-protein coupled receptor that is encoded by herpesviruses, especially CMV. US28 is a rare multi-chemokine family binding receptor with the ability to bind ligands such as CCL2/MCP-1, CCL5/RANTES, and CX3CL1/fraktalkine as ligands. Ligand binding to US28 activates cell-type and ligand-specific signalling pathways leading to cellular migration, which is an important example of receptor functional selectivity. Additionally, US28 has been demonstrated to constitutively activate Gαq, phospholipase C (PLC) and NF-kB signaling pathways, amongst others.

The term "extracellular loops", as is used herein, refers to the parts of the protein that are located on the outer side of a plasma membrane. Being a G-protein coupled receptor, US28 comprises 7 transmembrane domains and the extracellular loops comprise the N-terminal part in front of the first transmembrane domain, the part between the second and third transmembrane domains, the part between the fourth and fifth transmembrane domains, and the part between the sixth and seventh transmembrane domains.

The term "transmembrane domain", as is used herein, refers to a membrane-spanning protein domain. A transmembrane domain in general comprises non-polar and/or hydrophobic amino acid residues. The presence of a transmembrane domain can be predicted using, for example, hydrophobicity analysis. Computational resources are available, such as HMMTOP, TMpred, TMHMM and TopPred2, that may help in predicting transmembrane domains in protein sequences. The transmembrane domains of US28 are known and have been described in, for example, Rosenkilde et al., 2008. Brit J Pharm 153: S154-S166. Burg et al., 2015. Science 347: 1113-7.

The term "N-terminal extracellular region of US28" refers to the N-terminal region on US28 with the amino acid sequence N-terminus MTPTTTA/TELTTEFD/EYDD/E/LE/D/GATP, in which A/T, D/E, D/E/L and E/D/G indicate alternative amino acid residues at a position, as present in different HCMV strains.

The term "inverse agonist", as is used herein, indicates that binding of an antibody according to the invention to the receptor not only blocks the effects of agonist-binding, such as binding of CCL2/5 and/or CX3CL1, but also inhibits basal activity of the receptor through downstream pathways including NF-κB.

Anti-US28 VHHs

Described herein is a specific class of antibodies, namely single heavy chain variable domain antibody antibodies (VHH). The heavy chain variable domain antibodies were isolated from llamas and alpacas that were immunized with DNA constructs expressing US28 from HCMV. The camelids received a primary injection and at least one boost injection at 14 days after the primary injection, preferably 2-10 boost injections such as, for example, five boost injections.

Immune phage display libraries were generated from these animals 14 days after the last boost injection. These libraries were screened for binding to US28, and for their ability to displace a radiolabelled chemokine CCL5 (125I-CCL5) from US28-expressing cells. This resulted in the isolation of one VHH that fully inhibited the binding of radiolabelled CCL5 or CX3CL1 to US28.

Described herein is a single heavy chain variable domain antibody against human cytomegalovirus protein US28, which antibody binds to extracellular loops including, for example, an N-terminal extracellular region, of US28.

Said anti-US28 heavy chain variable domain antibody or VHH preferably has a binding affinity of at most $10^{-6}$ M, more preferred at most $10^{-7}$ M, more preferred at most $10^{-8}$ M, more preferred at most $10^{-9}$ M, more preferred at most $10^{-10}$ M.

A VHH according to the invention preferably comprises CDR1, CDR2 and CDR3 amino acid sequences XTGVA, preferably F/YTGVA for CDR1; XXTXDGXTX, preferably L/T/SI/T/ATG/NDGA/GTR/K for CDR2; and KTGXX, preferably KTGE/RY/F for CDR3, or a derivative thereof. Said CDR sequences preferably are present in a consensus framework region as presented in Table 1. Further preferred CDR sequences, and full length sequence of the variable VHH regions, are provided in Table 1. A most preferred VHH according to the invention comprises amino acid sequences FTGVA for CDR1, LITGDGATR for CDR2, and KTGEY for CDR3. A most preferred VHH according to the invention comprises amino acid sequences of VUN100 as indicated in Table 1.

A remarkable finding was that the identified VHHs, which originated from different lamas and were derived from different V-genes, are characterized by similar CDR1 and CDR3 sequences, and related CDR2 sequences. In addition, VHHs were found to act as antagonists of US28 as monovalent antibodies, and as inverse agonists of US28 as bivalent antibodies, which reduces constitutive US28 signaling. Hence, a preferred single heavy chain variable domain antibody binds to extracellular loops including, for example, an N-terminal extracellular region, of US28 and acts as an antagonistic or inverse agonistic antibody. Such antibody is very useful in the treatment of CMV-associated cancers such as colon cancer, breast cancer, ovarian cancer and glioblastoma.

A preferred derivative may comprise alterations of the amino acid sequence of the CDRs to increase their efficiency, affinity and/or physical stability including, for example a conservative derivative. The term "conservative derivative", as used herein, denotes the replacement of an amino acid residue by another, biologically similar residue. Examples of conservative derivatives include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like. The CDR sequences of a preferred derivate, preferably a conservative derivative, preferably are more than 80% identical, more preferably are more than 90% identical, more preferably are more than 95% identical to the amino acid sequences of CDR1, CDR2 and CDR3 indicated herein above, De-Immunization and Humanization of VHHs Although VHH antibodies hardly induce an immune response after administration to humans, de-immunization and/or humanization may be required for use of the VHH antibodies of the invention in pharmaceutical compositions. De-immunization is a preferred approach to reduce the immunogenicity of the anti-CMV VHH single heavy chain variable domain antibodies according to the invention. It involves the identification of linear T-cell epitopes in the antibody of interest, using bioinformatics, and their subsequent replacement by site-directed mutagenesis to non-immunogenic sequences or, preferably human sequences. Methods for de-immunization are known in the art, for example from WO098/52976.

A further preferred approach to circumvent immunogenicity of antibodies according to the invention when applied to humans involves humanization. Various recombinant DNA-based approaches have been established that are aimed at increasing the content of amino acid residues in antibodies that also occur at the same or similar position in human antibodies while retaining the specificity and affinity of the parental non-human antibody. Most preferred are amino acid residues that occur in antibodies as they are encoded by genomic germ line sequences.

Preferred methods for humanizing antibodies include grafting of CDRs (Queen et al., 1989. PNAS 86: 10029; Carter et al., 1992. PNAS 89: 4285; resurfacing (Padlan et. al., 1991. Mol Immunol 28: 489; superhumanization (Tan et. al., 2002. J Immunol 169: 1119), human string content optimization (Lazar et al., 2007. Mol Immunol 44: 1986) and humaneering (Almagro et. al., 2008. Frontiers Biosci 13: 1619). Further preferred methods are described in the published international applications WO2011080350; WO2014033252 and WO2009004065; and in Qu et al., 1999. Clin. Cancer Res. 5: 3095-3100; Ono et al., 1999. Mol. Immunol. 36: 387-395; These methods rely on analyses of the antibody structure and sequence comparison of the non-human and human antibodies in order to evaluate the impact of the humanization process into immunogenicity of the final product.

Humanization may include the construction of VHH-human chimeric antibodies, in which the VHH binding regions are covalently attached, for example by amino acid bonds, to one or more human constant (C) regions.

Anti-US28 Antibodies

The invention further provides an antibody, preferably a bispecific or multispecific antibody, comprising a single heavy chain variable domain that binds US28 according to the invention. Said antibody preferably comprises means for prolonging the biological half life of the single heavy chain variable domain, for example after administration of the single heavy chain variable domain to an individual. Said antibody may also comprise means for eliminating cells carrying US28 proteins on their surface via antibody-dependent cell-mediated cytotoxicity (ADCC) routes and/or complement dependent cytotoxicity (CDC) routes. For this, a single heavy chain variable domain that binds US28 according to the invention preferably is combined with an immunoglobulin Fc region.

In a preferred embodiment, said antibody comprises an immunoglobulin Fc region or functional part thereof of an immunoglobulin heavy chain. The Fc region or functional part thereof is preferably derived from IgG1, IgG2, IgG3, IgG4, IgM, IgD, IgA or IgE. It is further preferred that the Fc region or part thereof is a human Fc region or part thereof or a camelid Fc region or part thereof, for example a lama Fc region or part thereof. Said camelid Fc region or part thereof preferably is humanized. A single heavy chain variable domain is preferably connected to a Fc region or functional part thereof via a hinge region. A preferred hinge region is the hinge region of a camelid or human immunoglobulin heavy chain molecules from IgG1, IgG2, IgG3, IgG4, IgM, IgD, IgA or IgE, most preferred from IgG1. A hinge region of a camelid immunoglobulin heavy chain molecule preferably is humanized.

A preferred part of an Fc region is the region comprising the CH2 domain, the CH3 domain, or the CH2 and CH3 domains of IgGs, preferably IgG1 or IgG3, most preferably CH2 and CH3 domains of human IgG1.

A further preferred antibody is a bi- or multivalent antibody comprising an anti-US28 single heavy chain variable domain according to the invention. Said bi- or multivalent antibody preferably is a bispecific or multispecific antibody comprising two or more single heavy chain variable domains. Said single heavy chain variable domains may be the same, or different recognizing the same or different epitopes on a US28 molecule. A bi- or multivalent antibody preferably comprises two or more single heavy chain variable domains according to the invention. However, a VHH of the invention may be combined with other, preferably non-competing and non-interfering anti-US28 VHH.

Said two or more single heavy chain variable domains are preferably fused to the Fc region or part thereof, preferably comprising the C2 and C3 domains of IgGs, preferably IgG1 or IgG3, most preferably human C2 and C3 domains. The constant region that is fused to the single heavy chain variable domains preferably comprises a dimerization or multimerization motif. Alternatively, a bi- or multivalent antibody may be generated by chemical cross-linking or by a heterologous dimerization or multimerization domain comprising, for example, a leucine zipper or jun-fos interaction domain (Pack and Plückthun, 1992. Biochemistry 31, 1579-1584; de Kruif and Logtenberg, 1996. JBC 271: 7630-7634).

A further preferred bi- or multivalent antibody is a bihead or a multihead VHH, for example a trihead VHH, as described in WO2000/024884. The bihead or multihead antibodies preferably comprise a linking group which provides conformational flexibility so that each of the single heavy chain variable domains can interact with its epitope. A preferred linker group is a linker polypeptide comprising from 1 to about 60 amino acid residues, preferably from 10 to about 40 amino acid residues, most preferred about 35 amino acid residues such as 30 amino acid residues, 31 amino acid residues, 32 amino acid residues, 33 amino acid residues, 34 amino acid residues, 35 amino acid residues, 36 amino acid residues, 37 amino acid residues, 38 amino acid residues, or 39 amino acid residues. Some preferred examples of such amino acid sequences include Gly-Ser linkers, for example of the type (Gly Ser$_2$)$_3$ such as, for example, (Gly$_4$Ser)$_3$, (Gly$_4$Ser)$_7$ or (Gly Ser$_2$)$_3$, as described in WO 99/42077, and the GS30, GS15, GS9 and GS7 linkers described in, for example, WO 06/040153 and WO 06/122825, as well as hinge-like regions, such as the hinge regions of naturally occurring heavy chain antibodies or similar sequences (such as described in WO 94/04678).

An antibody according to the invention is preferably provided with means to extend the half life of the antibody after administration to a human individual. For example, said antibody may be coupled to a serum protein, such as human serum albumin (HSA). Said coupling may be direct or indirect coupling. A preferred multivalent antibody may comprise at least one anti-US28 VHH according to the invention and a VHH that interacts with an abundant antigen, preferably a VHH directed against a serum protein. For this, a VHH may be used that is directed against, for example, HSA.

An antibody according to the invention may be linked, chemically or otherwise, to one or more groups or moieties that extend the half-life of the antibody. Such groups or moieties include PolyEthleneGlycol (PEG) and HSA. General methods for coupling of antibodies are described in WO 2011/049449. Methods for PEGylating an antibody are known in the art, for example from U.S. Pat. No. 7,981,398. Said antibody in addition may be provided with means to cross the blood-brain barrier. Said mean include nanoparticles such as nanoparticles based upon poly(butylcyanoacrylate), poly(lactic-co-glycolic acid), poly(lactic acid), liposomes, and quantum dots. Said nanoparticles preferably are coupled to, for example, transferrin to mediate endocytosis of the coupled nanoparticles by the transferrin receptor at the luminal side, followed by movement through the endothelial cytoplasm and exocytosis at the abluminal (brain) side of the brain capillary endothelium.

Methods to Produce an Anti-US28 Antibody

An antibody as described, for example a single heavy chain variable domain or an antibody comprising a single heavy chain variable domain, may be produced using antibody producing prokaryotic cells or eukaryotic cells, preferably mammalian cells such as CHO cells or HEK cells, or fungi, most preferably filamentous fungi or yeasts such as *Saccharomyces cerevisiae* or *Pichia pastoris*, or mouse ascites. An advantage of a eukaryotic production system is that folding of the protein results in proteins that are more suitable for treating a human individual. Moreover, eukaryotic cells often carry out desirable post translational modifications that resemble posttranslational modifications that occur in mammalian cells.

Production of antibodies, especially of VHHs, in prokaryotic cells, preferably *Escherichia coli*, may be performed as described in Arbabi-Ghahroudi et al., 2005. Cancer Metastasis Rev 24: 501-519). Production of VHHs in bacteria such as *E. coli* can be performed by secretion of the antibody into the periplasmic space, or by expression in the reducing cytosol. The latter may require refolding of antibody fragments (Arbabi-Ghahroudi et al., 2005. Ibid.).

Production of antibodies in filamentous fungi is preferably performed as described by Joosten et al., 2005. J Biotechnol 120: 347-359, which is included herein by reference. A preferred method for producing antibodies in *Saccharomyces cerevisiae* is according to the method as described by van der Laar et al., 2007. Biotech Bioeng 96, 483-494; or Frenken et al., 2000. J Biotechnol 78: 11-21. Another preferred method of antibody production is by expression in *Pichia pastoris* as described by Rahbarizadeh et al., 2006. J Mol Immunol 43: 426-435.

A further preferred method for production of therapeutic antibody comprises mammalian cells such as fibroblasts, Chinese hamster ovary cells, mouse cells, kidney cells, human retina cells, or derivatives of any of these cells. A most preferred cell is a human cell such as, but not limited to, Hek293 and PER.C6. A further preferred cell line is a cell line in which alpha-(1,6)-fucosyltransferase has been inactivated, for example the ΔFUT8 CHO cell line, as described in Yamane-Ohnuki et al., 2004. Biotechnol Bioeng 87: 614-622. It was found that antibodies that are produced in ΔFUT8 cells enhance the ADCC route.

An antibody according to the invention is preferably produced by the provision of a nucleic acid encoding said antibody to a cell of interest. Therefore, described herein is a nucleic acid encoding an antibody according to the invention. Said nucleic acid, preferably DNA, is preferably produced by recombinant technologies, including the use of polymerases, restriction enzymes, and ligases, from the constructs encoding the single heavy chain variable domains that were isolated from the immunized animal, as is known to a skilled person. Alternatively, said nucleic acid is provided by artificial gene synthesis, for example by synthesis of partially or completely overlapping oligonucleotides, or by a combination of organic chemistry and recombinant technologies, as is known to the skilled person. Said nucleic acid is preferably codon-optimised to enhance expression of the antibody in the selected cell or cell line. Further optimization preferably includes removal of cryptic splice sites, removal of cryptic polyA tails and/or removal of sequences that lead to unfavourable folding of the mRNA. The presence of an intron flanked by splice sites may encourage export from the nucleus. In addition, the nucleic acid preferably encodes a protein export signal for secretion of the antibody out of the cell into the periplasm of prokaryotes or into the growth medium, allowing efficient purification of the antibody.

Further provided is a vector comprising a nucleic acid encoding an antibody according to the invention. Said vector preferably additionally comprises means for high expression levels such as strong promoters, for example of viral origin (e.g., human cytomegalovirus) or promoters derived from genes that are highly expressed in a cell such as a mammalian cell (Running Deer and Allison, 2004. Biotechnol Prog 20: 880-889; U.S. Pat. No. 5,888,809). The vectors preferably comprise selection systems such as, for example, expression of glutamine synthetase or expression of dihydrofolate reductase for amplification of the vector in a suitable recipient cell, as is known to the skilled person.

The invention further provides a method for producing an antibody, the method comprising expressing a nucleic acid encoding an antibody of the invention in a relevant cell and recovering the thus produced antibody from the cell. The nucleic acid, preferably a vector comprising the nucleic acid, is preferably provided to a cell by transfection or electroporation. The nucleic acid is either transiently, or, preferably, stably provided to the cell. Methods for transfection or electroporation of cells with a nucleic acid are known to the skilled person. A cell that expresses high amounts of the antibody may subsequently be selected. This cell is grown, for example in roller bottles, in fed-batch culture or continuous perfusion culture. An intermediate production scale is provided by an expression system comprising disposable bags and which uses wave-induced agitation (Birch and Racher, 2006. Advanced Drug Delivery Reviews 58: 671-685). Methods for purification of antibodies are known in the art and are generally based on chromatography, such as protein A affinity and ion exchange, to remove contaminants. In addition to contaminants, it may also be necessary to remove undesirable derivatives of the product itself such as degradation products and aggregates. Suitable purification process steps are provided in Berthold and Walter, 1994. Biologicals 22: 135-150.

Further provided is a host cell comprising a nucleic acid or vector that encodes an antibody according to the invention. Said host cell may be grown or stored for future production of an antibody according to the invention.

Utilization of an Anti-US28 Antibody

The invention further provides a product or composition comprising at least one anti-US28 antibody according to the invention. For this, the invention provides an antibody according to the invention for use as a medicament. The antibodies of the invention are preferably used for prophylactic administration or therapeutic administration in humans that are infected with CMV. Thus, antibodies according to the invention may be administered to an individual in order to lessen signs and symptoms of CMV infection, especially of a serious or even fatal CMV infection, or may be administered to an individual already evidencing active CMV infection, especially an individual with weakened immunity including a baby with congenital CMV infection.

An otherwise healthy individual suffering from an active CMV infection may have symptoms such as fatigue, fever, sore throat and/or muscle aches.

An individual with weakened immunity suffering from an active CMV infection may have signs and symptoms affecting eyes, lungs, liver, esophagus, stomach, intestines and/or brain. CMV infection in an individual with compromised immunity can be serious or even fatal. An individual who has undergone stem cell or organ transplants has an increased risk of suffering from a serious or fatal CMV infection.

Babies with congenital CMV infection may have signs and symptoms, including a low birth weight, yellow skin and eyes, enlarged and poorly functioning liver, purple skin splotches or a rash or both, abnormally small head, enlarged spleen, pneumonia and/or seizures.

An antibody according to the invention preferably is used in a medicament for treatment of an individual suffering from a CMV-associated tumor such as a glioblastoma. Said therapeutic anti-US28 antibody is preferably coupled to the human IgG1 Fc region, which can induce strong ADCC and CDC, when compared with the other heavy chain isotypes of a human antibody. A therapeutic antibody with a human IgG1 Fc region in addition may have a long-term stability in blood, when compared to antibodies having Fc regions from other immunoglobulins.

CMV infection, especially HCMV infection, is associated with enhanced angioproliferative and invasive phenotype of tumor cells such as colon cancer cell, breast cancer cells, ovarian cancer cells and glioblastoma cells. Anti-US28 antibodies, especially multivalent anti US28 antibodies, display inverse agonistic properties, reducing constitutive US28 signaling.

An antibody of the invention may be coupled to a cytotoxic drug. Said cytotoxic drug must contain a suitable functional group for conjugation to an antibody of the invention and is stable under physiological conditions. Said cytotoxic drug includes a microtubule inhibitor, a photosensitizer, a DNA-damaging agent and a polymerase II inhibitor such as α-amanitin.

For this, the antibody may be extended at the C-terminus, for example with a cysteine, to facilitate subsequent modification of the antibody. Said cytotoxic drug preferably is coupled through sulfhydryl-reactive chemical groups to said additional C-terminal cysteine. Said sulfhydryl-reactive chemical groups include maleimides, haloacetyls and pyridyl disulfides.

Said microtubule inhibitors include auristatins such as monomethyl auristatin E ((S)—N-((3R,4S,5S)-1-((S)-2-((1R,2R)-3-(((1S,2R)-1-hydroxy-1-phenylpropan-2-yl) amino)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino)butanamido)butanamide), and maytansinoids such as ansamitocin, mertansine (DM1; N2'-deacetyl-N2'-(3-mercapto-1-oxopropyl)-maytansine), and ravtansine/soravtansine (DM4).

Photosensitizers include, for example, aminolaevulinic acid and metal complexed with photosensitiser macrocycles such as metallochlorins and metallophthalocyanines.

DNA-damaging agents include anthracyclines, calicheamicins, duocarmycins, and pyrrolobenzodiazepines, which act by binding the minor groove of DNA and causing DNA stand scission, alkylation, and/or cross-linking.

The administration of an antibody according to the invention is preferably provided in an effective amount to an individual in need thereof. An effective amount of an antibody of the invention is a dosage large enough to produce the desired effect in which the symptoms of the CMV infection are ameliorated or the likelihood of infection is decreased. A therapeutically effective amount preferably does not cause adverse side effects, such as hyperviscosity syndrome, pulmonary edema, congestive heart failure, and the like. Generally, a therapeutically effective amount may vary with the individual's age, condition, and sex, as well as the extent of the disease and can be determined by one of skill in the art. The dosage may be adjusted by the individual physician or veterinarian in the event of any complication. A therapeutically effective amount may vary from about 0.01 mg/kg to about 500 mg/kg, preferably from about 0.1 mg/kg to about 200 mg/kg, most preferably from about 0.2 mg/kg to about 20 mg/kg, in one or more dose administrations daily, for one or several days. Preferred is administration of the antibody for 2 to 5 or more consecutive days in order to avoid "rebound" of virus replication from occurring.

An antibody according to the invention can be administered by injection or by gradual infusion over time. The administration of antibodies preferably is parenteral such as, for example, intravenous, intraperitoneal, intranasal, or intramuscular. Preparations for parenteral administration include sterile aqueous or non-aqueous solutions suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention further provides a pharmaceutical composition comprising an antibody according to the invention. A pharmaceutical composition preferably comprises a pharmaceutically acceptable carrier. A carrier, as used herein, means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts buffers, stabilizers, solubilizers, and other materials which are well known in the art.

An anti-US28 antibody according to the invention may further be used for diagnostic applications. An anti-US28 antibody of the invention may be labeled by a variety of means for use in diagnostic applications. There are many different labels and methods of labeling known to those of ordinary skill in the art. Examples of the types of labels which can be used include enzymes, radioisotopes, fluorescent compounds, colloidal metals, chemiluminescent compounds, infrared dyes, and bioluminescent compounds.

For in vivo diagnosis, radioisotopes may be bound to an antibody either directly or indirectly by using an intermediate functional group. Intermediate functional groups which are often used to bind radioisotopes which exist as metallic ions are the bifunctional chelating agents such as diethylenetriaminepentacetic acid (DTPA) and ethylenediaminetetra-acetic acid (EDTA) and similar molecules.

Typical examples of metallic ions which can be bound to the anti-US28 antibodies of the invention are $^{111}$Indium, $^{97}$Rubidium, $^{67}$Gallium, $^{68}$Gallium, $^{72}$Arsenic, $^{89}$Zirconium and $^{201}$Titanium.

An antibody of the invention can also be labeled with an infrared dye or with a paramagnetic isotope for purposes of in vivo diagnosis as in, for example, magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gadolinium, $^{55}$Manganes, $^{162}$Dysprosium, $^{52}$Chromium and $^{56}$Iron. Those of ordinary skill in the art will know of other suitable labels for binding to the antibodies of the invention, or will be able to ascertain such, using routine experimentation. Furthermore, the binding of these labels to the antibodies of the invention can be done using standard techniques common to those of ordinary skill in the art.

Another labeling technique which may result in greater sensitivity consists of coupling the antibodies to low molecular weight haptens. These haptens can then be specifically altered by means of a second reaction. For example, it is common to use haptens such as biotin, which reacts with avidin, or any one of dinitrophenol, pyridoxal, or fluorescein, which can react with specific anti-hapten antibodies.

An antibody of the invention may further be used in vitro, for example, in immunoassays in which it can be utilized for detection of antigens in liquid phase or bound to a solid phase carrier. The antibodies in these immunoassays can be detectably labeled in various ways. Examples of types of immunoassays which can utilize the antibodies of the invention are competitive and non-competitive immunoassays. The assays either comprise a direct or an indirect format and include radioimmunoassay (RIA) and the sandwich assay. CMV present in biological fluids and tissues can be detected by antibodies of the invention. A sample can be a liquid such as urine, saliva, cerebrospinal fluid, blood serum or the like; a solid or semi-solid such as tissues, feces, or the like; or alternatively, a solid tissue such as those commonly used in histological diagnosis.

Preferred antibodies according to the invention comprise a detectable label selected from the group consisting of a fluorescent label, a luminescent label, a (radio)isotope label, a paramagnetic label, a (bio)nanoparticle label, or a combination of two or more of said labels or a hybrid thereof.

A luminescent label preferably is a label with excitation and emission in the 200-1000 nm range. Particularly preferred is a fluorescent label. Said fluorescent or fluorescent hybrid label preferably is a label with excitation and emission in the 400 nm-1000 nm range. Non-limiting examples of fluorescent labels that can be attached to an antibody according to the invention are Abz (Anthranilyl, 2-Aminobenzoyl), N-Me-Abz (N-Methyl-anthranilyl, N-Methyl-2-Aminobenzoyl), FITC (Fluorescein isothiocyanate), 5-FAM (5-Carboxyfluorescein), 6-FAM (6-Carboxyfluorescein), TAMRA (Carboxytetramethyl rhodamine), Mca (7-Methoxycoumarinyl-4-acetyl), AMCA or Amc (Aminomethylcoumarin Acetate), Dansyl (5-(Dimethylamino) naphthalene-1-sulfonyl), EDANS (5-[(2-Aminoethyl) amino]naphthalene-1-sulfonic acid), Atto (e.g. Atto465, Atto488, Atto495, Atto550, Atto647), cyanine (Cy) dyes, including Cy3 (1-(5-carboxypentyl)-3,3-dimethyl-2-((E, 3E)-3-(1,3,3-trimethylindolin-2-ylidene)prop-1-en-1-yl)-3H-indol-1-ium chloride), Cy5 (1-(5-carboxypentyl)-3,3-dimethyl-2-((1E,3E,5E)-5-(1,3,3-trimethylindolin-2-ylidene) penta-1,3-dienyl)-3H-indolium chloride), including trisulfonated Cy5, and Cy7 (1-(5-carboxypentyl)-2-[7-(1-ethyl-5-sulfo-1,3-dihydro-2H-indol-2-ylidene)hepta-1,3,5-trien-1-yl]-3H-indolium-5-sulfonate), Alexa Fluor (e.g. Alexa Fluor 647, Alexa488, Alexa532, Alexa546, Alexa594, Alexa633, Alexa647), Bodipy (e.g. Bodipy® FL), Dylight (e.g. DyLight 488, DyLight 550), Trp (Tryptophan), *Lucifer Yellow* (ethylene diamine or 6-amino-2-(2-amino-ethyl)-1, 3-dioxo-2,3-dihydro-1H-benzo[de]isoquinoline-5,8-disulfonic acid) and derivatives thereof. Alternatively, inorganic dyes or dyes with a relatively long luminesce lifetime may be used e.g. quantum dots, silver/gold-particles, or luminescent transition metal complexes.

A detectable imaging label, preferably a label comprising a fluorescent moiety, is preferably directly bound an antibody according to the invention using known techniques in conjugation chemistry. Such labels can be inserted at the distal ends of the peptide sequences using known conjugation techniques e.g. click-chemistry.

The detectable imaging label may be attached to the antibody via a linker using know techniques in conjugation chemistry. A linker is for example suitable when using a (bio)nanoparticle label. Examples of such linkers are carbon linkers, peptide linkers and polyether linkers. These linker have functional groups, such as amide, alkyl halide and carboxylic acids, which can be used to form a bond with both the label and the antibody. Linkers can also be dendritic in nature allowing the grafting of one ore more imaging labels to one peptide sequence, or vice versa.

Imaging labels can be detected using any suitable method known in the art. For instance, a fluorescent label can be detected by exciting the fluorophore with the appropriate wavelength of light and detecting the fluorescence. Such detection can for instance be done using e.g. a microscope or an endoscope provided with a suitable excitation and emission settings for the fluorescent label used.

For the purpose of clarity and a concise description, features are described herein as part of the same or separate embodiments, however, it will be appreciated that the scope of the invention may include embodiments having combinations of all or some of the features described.

TABLE 1

Amino acid sequences of isolated VHHs
(Kabat numbering as applied for VHHs, according to Riechmann and Muyldermans,
1999 (Riechmann and Muyldermans, 1999. J Immunol Methods 23: 25-38).

```
                 1         10        20      ** 30     35    * 40          50
VUN100     EVQLVESGGGLVQPGGSLRLACAVSGPGLIFK  FTGVA  WYRPQVPGAKRGLVA  LITGDGATR

US28-Nb1   EVQLVESGGGLVQAGGSLRLSCVVSGT--IFS  YTGVA  WYR-QTSGKQREWVA  TTTNDGGTK

US28-Nb2   EVQLVESGGGLVQAGGSLRLSCVVSGT--IFS  YTGVA  WYR-QTSGNQREWVA  TATNDGGTK

US28-Nb3   EVQLVESGGGLVQAGGSLRLSCVVSGT--IFS  YTGVA  WYR-QTSGNQREWVA  SATNDGGTK

US28-Nb4   EVQLVESGGGLVQAGGSLRLSCVVSGT--IFS  YTGVA  WYR-QPSGKQREWVA  SATNDGGTK 60        70        80        90    96  103        113
VUN100          YGDSVKGRFTVSRDIAAKRVYLEMNDLRSEDTAVYYC  KTGEY  WGQGTQVTVSS

US28-Nb1        FADSVKGRFTISRDNAKKTVYLQMNNLNAEDTAVYYC  KTGRF  WGRGTLVTVSS

US28-Nb2        FADSMKGRFTISRDNAKKTVYLQMNNLNAEDAAVYYC  KTGRF  WGRGTLVTVSS

US28-Nb3        FADSVKGRFTISRDNAKKTVHLQMNNLNAEDAAVYYC  KTGRF  WGRGTLVTVSS

US28-Nb4        FADSVKGRFTISRDNAKKTVYLQMNNLDADDTAVYYC  KTGRF  WGRGTLVTVSS
```

Consensus
EVQLVESGGGLVQXGGSLRLXCXVSGXXXIFX XTGVA WYRXQXXGXXRXXVA XXTXDGXTX
XXDSVKGRFTXSRDXAXKXVYLXMNXLXXEDTAVYYC KTGXX WGXGTXVTVSS Consensus:
FR1        EVQLVESGGGLVQA/PGGSLRLS/ACV/AVSGT/PG/-L/-IFS/K

CDR1       Y/FTGVA

FR2        WYRR/-QT/VS/PGK/AQ/KRE/GW/LVA

CDR2       T/LT/ITN/GDGG/ATK/R

FR3        F/YA/GDSVKGRFTI/VSRDN/IAK/AKT/RVYLQ/EMNN/DLN/RA/SEDTAVYYC

CDR3       KTGR/EF/Y

FR4        WGR/GGTL/QVTVSS

* Inserted amino acid in framework region

Further described is an antibody that effectively competes with an anti-US28 antibody of the invention for binding to the epitope on the N-terminal extracellular domain of US28, said epitope preferably comprising the N-terminal extracellular region of US28 and the third extracellular loop of US28. The term effectively is used to indicate that the competing antibody binds with substantially the same affinity to the epitope, when compared to the antibody of the invention. The term substantially is used to indicate that the difference in affinity between an antibody of the invention and a competing antibody is preferably less than 10-fold, more preferred less than 5-fold, more preferred less than 2-fold, more preferred less than 1.5 fold. A preferred competing antibody is capable of effectively competing with an antibody of the invention when the competing antibody lowers the affinity of the observed binding of an antibody of the invention to its epitope about 2-fold using the same molar amount of competing antibody. Assays for measuring competition are known in the art and include, for example, competitive ELISA.

EXAMPLES

Example 1

Materials and Methods
Reagents
Human chemokines CCL5 and CX3CL1 were obtained from PeproTech, Rocky Hill, NJ, USA. Dulbecco's modified Eagle's medium (DMEM), Dulbecco's Phosphate-buffered saline (D-PBS), trypsin-EDTA and Poly-L-lysine solution were obtained from Sigma-Aldrich, Saint Louis, MO, USA. Fetal bovine serum (FBS) and penicillin/streptomycin were obtained from PAA Laboratories GmbH, Cölbe, Germany. 125I-Na and myo-[2-3H] inositol (1 mCi/ml) were obtained from Perkin Elmer Life Sciences, Waltham, MA, USA. Mouse anti-cytomegalovirus (immediate early antigen; MAB180R) was obtained from Merck Millipore, Billerica, MA, USA. Polyclonal rabbit-anti-US28 antibodies were generated by Covance (Princeton, NJ, USA) as described previously (Bongers et al., 2010. J Clin Invest 120: 3969-

78). Anti-Myc tag (clone 9B11, #2276) was obtained from Cell Signaling Technology, Danvers, MA, USA. Horseradish peroxidase (HRP)-conjugated antibodies (U.S. Pat. Nos. 1,706,515 and 1,706,516) were obtained from Bio-Rad Laboratories, Hercules, CA, USA. Alexa Fluor-conjugated antibodies (A11001, A11003, A11008 and A11010) were obtained from Thermo Fisher Scientific, Waltham, MA, USA.

Cell Lines and Cell Culture

HEK293T, NIH 3T3, U251-MG and, COS7 cells were previously described (Slinger et al., 2010. Ibid.; Casarosa et al., 2003. JBC 278: 5172-8). The U251 cell line was authenticated by STR profiling (Baseclear B. V., Leiden, The Netherlands). NIH 3T3 cells stably expressing US28-WT were described previously (Maussang et al., 2006. Ibid.). Cell lines with constitutive Fluc/mCherry (FM) expression and/or inducible US28 expression (U251-iUS28) were generated by lentiviral transduction. US28 expression was induced by 1 µg/mL doxycycline (D9891, Sigma-Aldrich). HFFF TR cells (Stanton et al., 2010. J Clin Invest 120: 3191-208) were kindly provided by Dr. Richard J. Stanton. All cell lines were *mycoplasma* negative (PCR testing, Microbiome, Amsterdam, The Netherlands). The primary GBM48 cells were obtained from a patient with glioblastoma multiform IV (GBM) at the Karolinska Institute and were cultured in DMEM/F12 medium with 10% (v/v) heat-inactivated FBS.

Generation of Spheroids and Neurospheres

Spheroids were generated by seeding $3 \times 10^4$ U251 cells per well in a 96-well hanging drop plate (3D Biomatrix, Ann Arbor, MI, USA). After 48 hours of sedimentation, spheroids were transferred to 6-well plates coated with 0.75% agarose in normal growth medium. Spheroids were imaged after 72 hours. GBM48 neurospheres were generated as described previously (Caretti et al., 2014. Acta Neuropathol 127: 897-909). GBM48 cells were infected with HCMV 24 hours before neurosphere formation and neurospheres were imaged 7 days post infection.

Microscopy Imaging

Immunofluorescence staining and microscopy imaging were performed as previously (Slinger et al., 2010. Ibid.; de Wit et al., 2017. J Pharmacol Exper Therap 363: 35-44). All images were obtained using an FSX-100 microscope (Olympus, Tokyo, Japan) at either 4× (spheroids or neurospheres) or 20× magnification (cells).

Molecular Cloning, Transfection and Transduction

The pcDEF3 plasmid encoding US28-WT (from HCMV strain VHL/E, GenBank: L20501.1) was described previously (Casarosa et al., 2001. JBC 276: 1133-752). HEK293T and COS7 cells were transfected using linear 25 kDa polyethylenimine (PEI; Polysciences Inc., Warrington, PA, USA) (Casarosa et al., 2001. Ibid.). For lentiviral transduction, the US28 DNA was subcloned in the pLenti6.3/To/V5-DEST vector. Lentivirus was produced for 48 hours upon co-transfection of HEK293T cells with CMV Fluc-IRES-mCherry, US28-VHL/E pLenti6.3/To/V5-DEST or pLenti3.3/TR (Thermo Scientific) together with pRSV-REV, pMDLg/pRRE and pMD2.g packaging vectors. Lentivirus solution was cleared by centrifugation and filtration and cells were transduced overnight.

HCMV Infection

The HCMV strain TB40/E WT and the deletion mutant TB40/E ΔUS28 were previously described (Langemeijer et al., 2012. PloS one 7: e48935). HCMV strain Merlin was generated from a bacterial artificial chromosome BAC pAL2157. This is BAC pAL1498 (Stanton et al., 2010. Ibid.) in which eGFP was linked to the IE2 gene using a P2A linker. SW102 *E. coli* containing BAC pAL2157 were kindly provided by Dr. Richard J. Stanton. BAC DNA was isolated using NucleoBond Xtra BAC kit (Macherey Nagel, Duren, Germany). Virus production was initiated by electroporation of BAC DNA into HFFF TR cells using the Amaxa Nucleofector and the basic fibroblast nucleofector kit (Lonza, Basel, Switserland). Subsequent virus productions in HFFF TR cells were started with an infection at MOI 0.02 and titres were determined after 3 days using immediate early antigen staining. U251 and GBM48 GBM cells were infected at MOI 3.

Generating VHHs

US28 cDNA encoded by VHL/E strain (GenBank: L20501.1) was subcloned from pcDEF3 to pVAX1 (Thermo Fisher Scientific). One llama and one alpaca were immunized 4 times with pVAX1-US28 DNA, followed by boost immunizations with HEK293T cells expressing US28. Subsequently, VHH phage-libraries were generated as previously (Jahnichen et al., 2010. Ibid.) and phage-display selections were performed on US28-expressing virus-like particles (Integral Molecular, Philadelphia, PA, USA) and US28-expressing COS7 membrane extracts. VHH clones were screened for displacement of 125I-CCL5 (100 pM) using *E. coli* periplasmic extracts. Hits showed a 3×SD-value reduction in ligand binding. A bivalent VHH construct was generated via a genetic head-to-tail fusion of two identical VHHs, separated by a 35 GS-linker (i.e. 7 GGGGS-repeats). VHHs were produced and purified from BL21 *E. coli* (de Wit et al., 2017. Ibid.). Half-life extended VHHs were produced in *Pichia pastoris* strain XL-33 (Maussang et al., 2013. Ibid.).

Binding Assays

Displacement and cell-surface binding of 125I-labeled chemokines CCL5 or CX3CL1 (Casarosa et al., 2001. Ibid.; Casarosa et al., 2003. Ibid.) was analyzed using a Competitive One-Site binding fit and Competitive One-Site Fit-LogIC50 binding fit respectively. Displacement of radiolabeled chemokines with 10-6 M of unlabeled CX3CL1 was taken as full displacement. Flow cytometry was performed as described previously (de Wit et al., 2017. Ibid.).

US28 Signaling Assays

Activation of phospholipase C was determined by quantification of the [3H]-inositol phosphates (InsP) (Slinger et al., 2010. Ibid.). NFκB-luciferase reporter gene assays were performed in HEK293T cells (Casarosa et al., 2003. Ibid.) and luminescence (1 second per well) was measured with a Mithras LB940 multilabel plate reader (Berthold Technologies). VEGF levels were measured in conditioned medium by ELISA using the Quantikine human-VEGF ELISA kit (R&D systems) (de Wit et al., 2016. Ibid.). In all VEGF ELISA assays, the lower detection limit was 15 pg/ml.

Foci Formation and Proliferation Assay

The US28-dependent formation and growth of foci was assessed in NIH 3T3 cells (Slinger et al., 2010. Ibid.; Burger et al., 1999. J Immunol 163: 2017-22). Methylene blue-stained foci was quantified using ImageJ software. Cell proliferation of NIH 3T3 cells was quantified by total protein yield as determined by BCA assay (Bio-Rad).

Immunohistochemistry

Paraffin-embedded animal (8 µm) and patient (5 µm) tissue sections were deparaffinized in tissue clear (Sakura) and rehydrated via a graded ethanol series. Antigen retrieval was performed using a high pressure cooker (Decloaking Chamber NxGEN) in DIVA decloacker (Biocare Medical) solution (12 minutes at 95° C.). Hereafter, incubation with pepsin (Sigma-Aldrich) (5 minutes at 37° C.), peroxidazed-1 (Biocare Medical) (3 minutes at 20° C.), background sniper (Biocare Medical) (15 minutes at 20° C.), and protein block (DAKO) (10 minutes at 20° C.) was performed. Primary antibody incubation with polyclonal rabbit anti-US28, 1:500 for animal tissue and 1:700 for GBM patient tissue (Covance) at 4° C. was performed overnight. MACH2 Universal HRP-Polymer Detection (Biocare Medical) served as secondary antibody. VHH staining was performed using similar methods: bivalent US28-Nb incubation overnight was followed by incubation with 1:500 mouse anti-Myc antibody (Cell Signaling) (1 hour at 20° C.). From here on, Tyramide Signal Amplification (TSA) was used following manufacturers protocol. Sections were developed using 3,3'-diaminobenzidine (DAB) (Biocare Medical) and counterstained with aqua hematoxylin (Innovex). Finally, sections were dehydrated via graded ethanol series and xylene, and mounted using DPX neutral mounting medium (KliniPath). The study was approved by the Stockholm's Regional ethical committee (permission number: 2008/628-31/2) in Sweden.

Animal Model Studies

All animal experiments were conducted in compliance with Dutch Law on animal experimentation and the European Community Council Directive 2010/63/EU for laboratory animal care and approved by the animal experimentation commission of the VU University Medical Center. The required sample sizes were calculated based on in vitro data and a small in vivo pilot using a two-sided t-test, significance level (Type I error) of 0.05, power of 0.9 and assuming a 50% difference between sample means and a 20% standard deviation in both groups. 6 weeks old female athymic nude mice (Harlan/Envigo, Horst, The Netherlands) were kept as described previously (Jansen et al., 2016. Mol Cancer Ther 15: 2166-2174). With the exception of the initial US28 comparison study (3 mice/group), studies were performed with 6 mice/group. Stereotactic injections were performed with 5-10$^5$ cells as described previously (Jansen et al., 2016. Ibid.). Mice were monitored daily and tumor development was monitored twice weekly using an IVIS/CCD camera (Caliper Life Sciences, Waltham, MA, USA) or In-Vivo Extreme imager (Bruker, Billerica, MA, USA) upon intraperitoneal injection of D-luciferin (150 mg/kg, GoldBio, Olivette, MO, USA). Mice were fed sucrose water (5% w/v) or doxycycline/sucrose-water (2 mg/mL, 5% w/v). Mice were stratified by tumor size and treated three times per week with PBS or VHHs (500 µg) via intraperitoneal injections. No blinding was used. Mice were sacrificed upon >15% weight loss, blood was drawn via cardiac puncture and brains were formalin-fixed.

Magnetic Resonance Imaging

Magnetic resonance imaging (MRI) was performed using a preclinical PET-MRI system (Nanoscan system, Mediso, Budapest, Hungary) (Jansen et al., 2016. Ibid.). A T1 weighed scan was performed before and after injection of 750 µmol of the MRI contrast agent Gadolinium (Dotarem) in the tail vein using a cannula. MRI images were analyzed using MIPAV software (Medical Image Processing, Analysis, and Visualization, version 7.2.0).

Statistical Analyses

Unless indicated otherwise, all data represented three independent experiments, each performed in triplicates. Data and error bars represent mean SEM. Acquisition and analysis of data regarding spheroids, neurospheres and bioluminescence was blinded. Graphs and statistical analyses were performed with Prism 6 (GraphPad software Inc. San Diego, CA, USA). Groups were compared using student's t test (two-tailed, significance level of α=0.05) or ANOVA analyses with multiple comparisons test and Tukey correction. Normality of data was determined using the D'Agostino-Pearson omnibus test. Equality of variance was confirmed with an F test. No data was excluded.

Results

HCMV-Encoded Chemokine Receptor US28 Enhances GBM Growth

Figure 1:
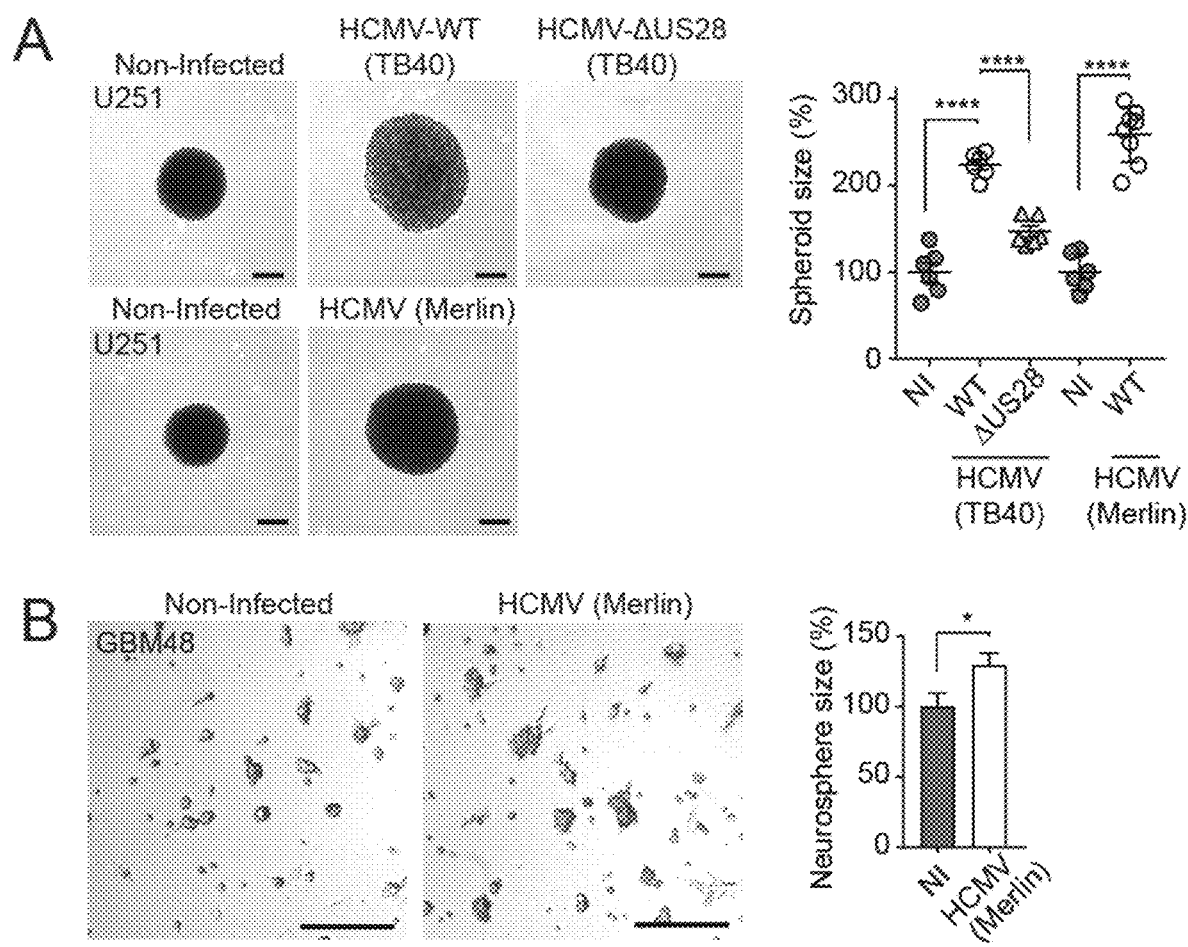
FIG. 1: US28 mediates HCMV-enhanced GBM growth. (A) Representative spheroids and spheroid size of uninfected U251 cells, or U251 cells infected with HCMV strain TB40/E wild type, HCMV in which US28 was deleted (HCMV-ΔUS28) or strain Merlin wild type. Spheroids were generated using the hanging droplet method followed by culture on 0.75% agarose (n=6 spheroids per group). (B) Neurospheres of GBM48 primary GBM cells upon infection with HCMV strain Merlin (n=>80 neurospheres per group). Representative plots are shown. All scale bars represent 250 μm. Sizes of individual spheroids or neurospheres are plotted as percentages of non-infected with mean±SEM. *$P<0.05$, ****$P<0.0001$ (unpaired t-test).
Figure 2:
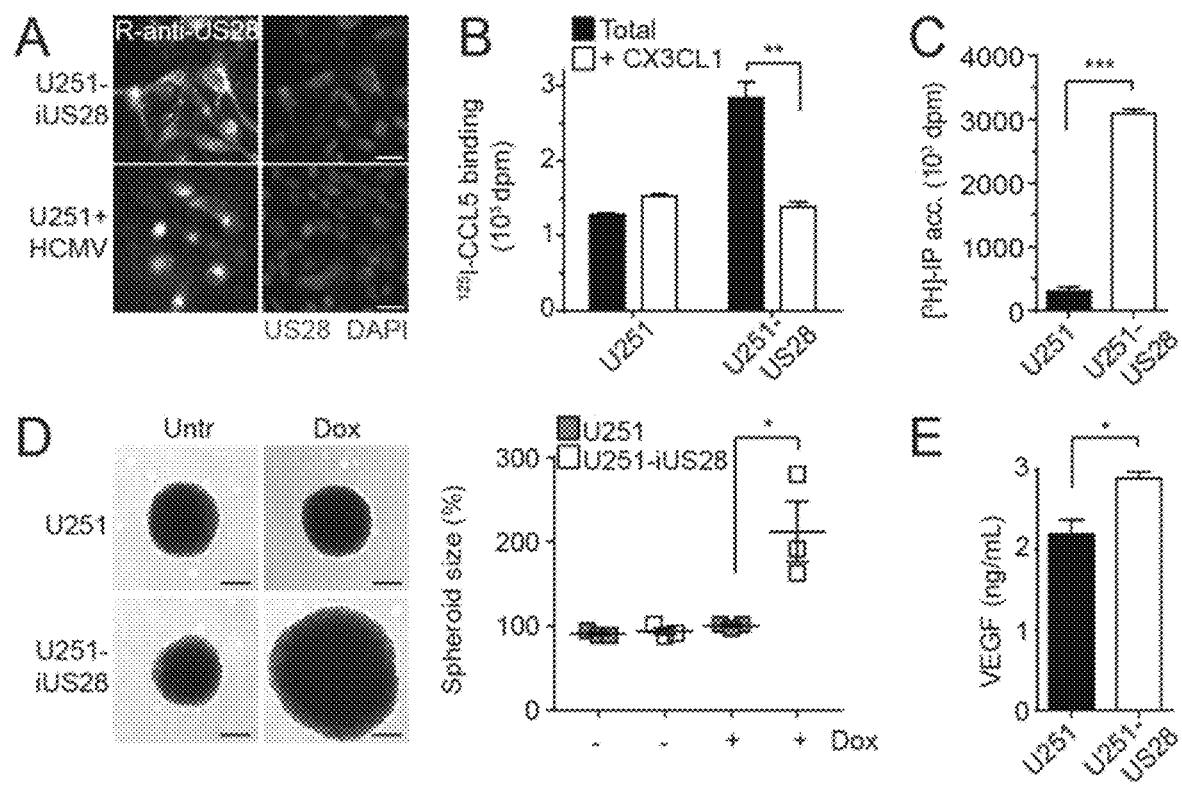
FIG. 2: US28 signalling in enhances growth of GBM spheroids. (A) Inducible expression of US28 in U251-iUS28 cells. Expression of US28 was induced with doxycycline. Bottom panel shows US28 expression in HCMV Merlin-infected U251 cells. US28 was stained in fixed/permeabilized cells using polyclonal rabbit-anti-US28 antibodies directed against the C-terminus of US28. Scale bars represent 20 μm. (B) Whole cell binding of 125I-CCL5 to U251-iUS28 cells shows membrane expression of US28 upon induction with doxycycline. Specific displacement of 125I-CCL5 was performed with an excess of CX3CL1. (C) Constitutive US28-mediated PLC activation U251-iUS28 cells upon induction of US28 expression as subsequently determined by inositol phosphate ([3H]-IP) accumulation. (D) US28 expression in U251-iUS28 cells induces growth of GBM spheroids. Spheroids were generated by the hanging droplet method. A representative graph of spheroid size quantification is shown. Individual spheroid sizes are plotted as percentages with mean SEM (n=6 spheroids per group). (E) Spheroids from U251-iUS28 cells secrete VEGF upon induction of US28 expression. Data shows mean±SEM. *$P<0.05$, $P<0.01$, *$P<0.001$ (unpaired t-test).

Infection of U251 MG GBM cells with HCMV (strain TB40/E) significantly enhanced the size of 3D spheroids (FIG. 1A). This HCMV-induced growth was significantly reduced when these cells were infected with a HCMV variant in which US28 was deleted (HCMV-ΔUS28), despite comparable infection rates (data not shown). This observation suggests a key role for US28 in the oncomodulatory properties of HCMV in these GBM cells. Infection of these cells with the clinically more relevant HCMV strain Merlin resulted in a significant enhancement of U251 spheroid size (FIG. 1A) and neurospheres of GBM48 primary GBM cells (FIG. 1B). To study the role of US28 in GBM tumor development in vitro and in vivo in more detail, we established a doxycycline-inducible US28 GBM cell line (U251-iUS28) and developed an orthotopic intracranial GBM model in mice using this cell line. After induction of gene expression, US28 protein levels were confirmed using fluorescence microscopy and specific 125I-CCL5 binding (FIGS. 2A and B). In line with previous studies, doxycycline-induced US28 expression resulted in a significantly enhanced intracellular accumulation of inositol phosphates (IP) (FIG. 2C) (Slinger et al., 2010. Ibid.). Moreover, US28 expression significantly enlarged U251 spheroids (FIG. 2D), accompanied with an increase in VEGF secretion (FIG. 2E). This data confirms that US28 exhibits oncomodulatory signaling properties in GBM cells in vitro (de Wit et al., 2016. Ibid.).

Figure 3:
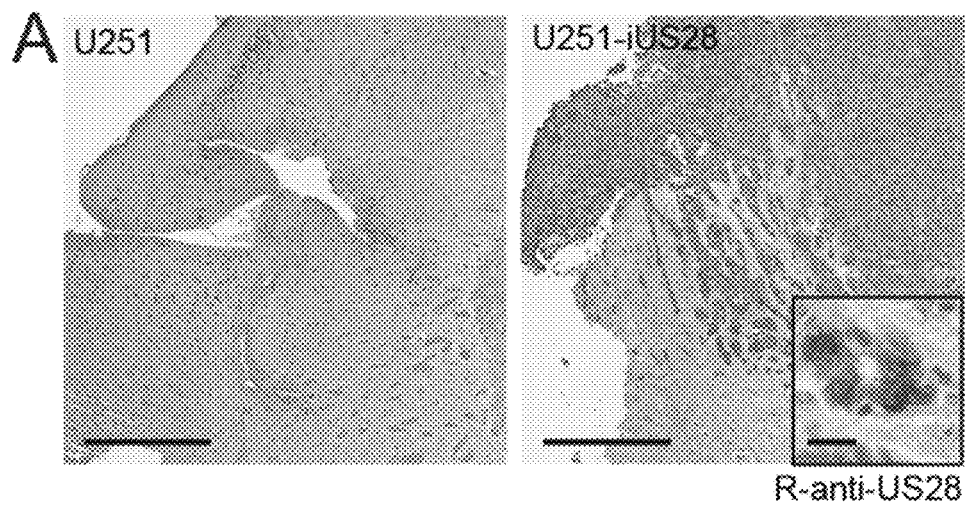
FIG. 3: Constitutive activity of US28 enhances GBM growth. (A) Sections of paraffin-embedded brains from US28-expressing orthotopic GBM model in mice, stained with hematoxylin and rabbit-anti-US28 antibodies. Scale bars represent 100 μm (large panels) or 30 μm (small panel). (B-D) Orthotopic GBM model generated with inducible U251-FM-iUS28 cells or parental U251-FM cells in striatum in mice. (B and C) In vivo tumor growth as quantified by bioluminescence imaging (n=6 mice per group). (D) US28-positive tumors were externally visible (arrow).
Figure 3:
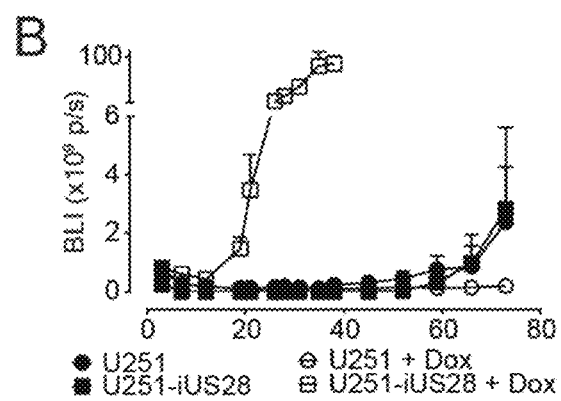
Figure 3:
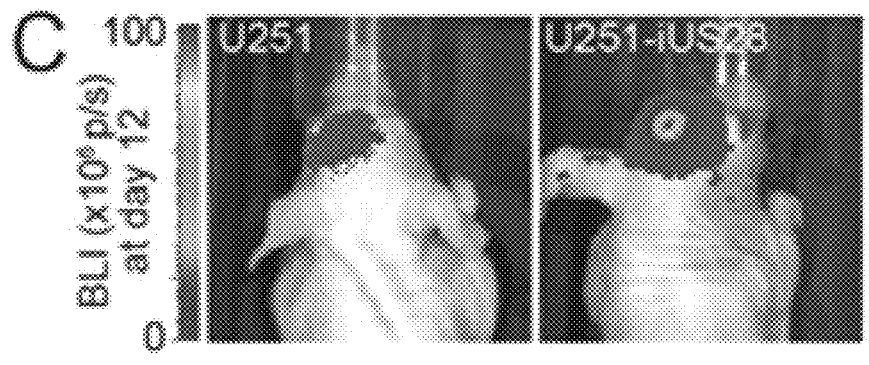
Figure 3:
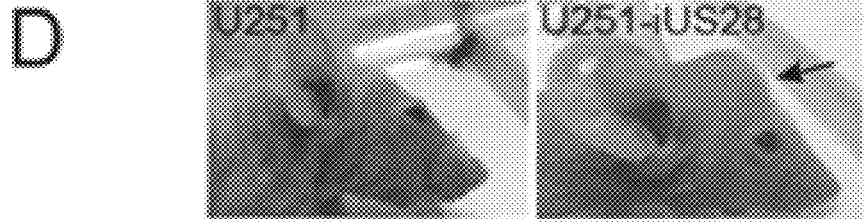

In order to study this phenotype in vivo, U251 and U251-iUS28 lines constitutively expressing firefly luciferase/mCherry (FM) were generated to allow in vivo tumor size quantification via bioluminescent imaging (BLI) (Wurdinger et al., 2008. Nat Methods 5: 171-3). These U251-FM-iUS28 cells showed similar increases in IP signaling (data not shown) and were subsequently used in an orthotopic GBM model in the striatum of mice brains (FIG. 3A-D). The inducible expression of US28 in these brain tumors was confirmed by immunohistochemistry on paraffin-embedded brain tissue sections (FIG. 3A). While control and non-induced tumor expansion initiated approximately 40 days after surgery, growth of US28-expressing tumors was already evident after 10 days and showed a significantly accelerated rate of tumor growth (FIG. 3B). The US28-enhanced growth was also apparent by a clear invasive and extracranial tumor growth (FIGS. 3C and 3D), which are obvious signs of a more aggressive tumor phenotype. These data indicate that US28 expression accelerates GBM tumor growth.

Generation of US28-Targeting VHHs

Figure 4:
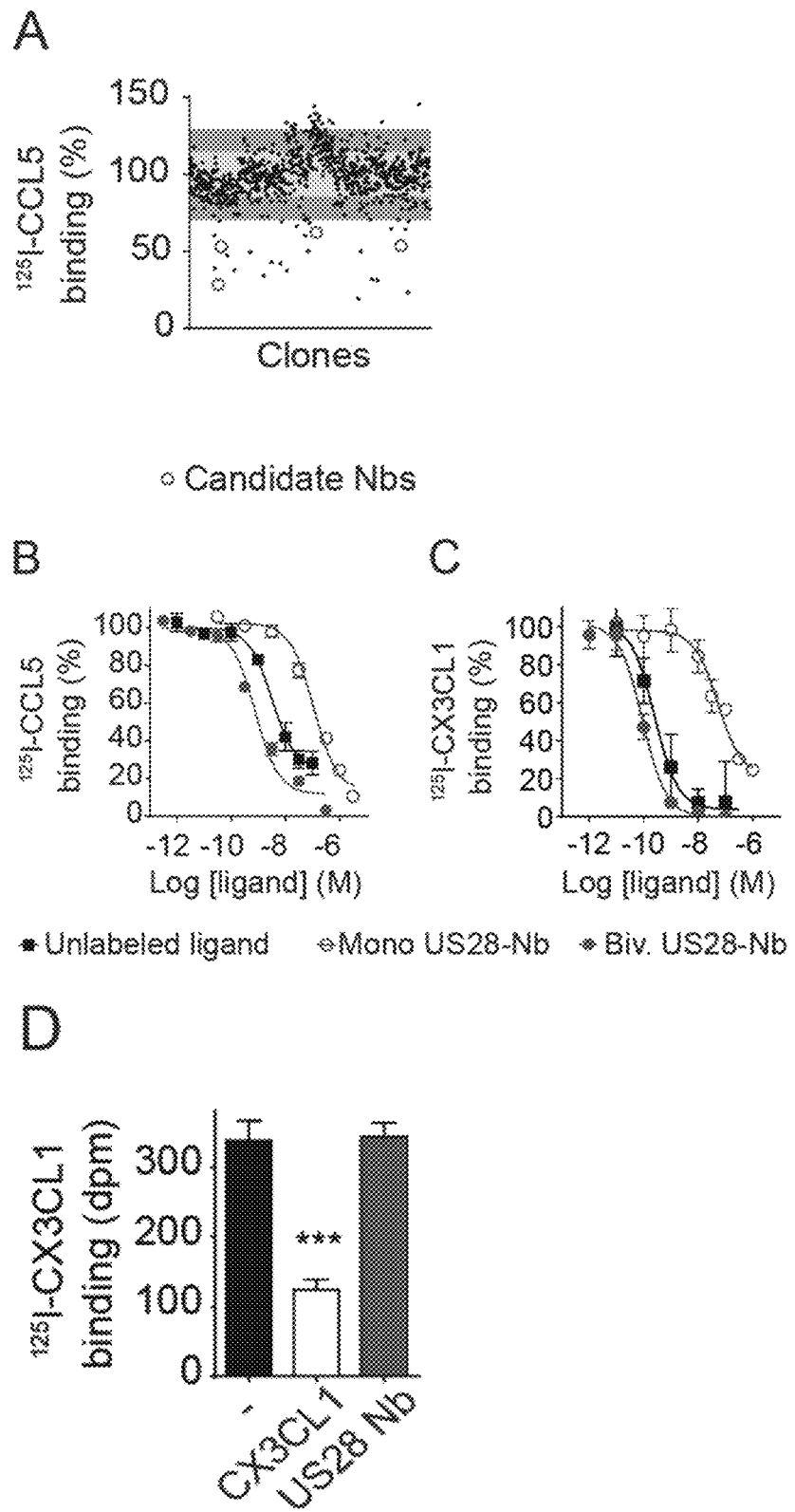
FIG. 4: US28-targeting VHHs displace chemokine binding. (A) Displacement of 125I-CCL5 from US28-expressing HEK293T membranes by periplasmic extracts expressing single VHH clones. Candidate clones are indicated with open circles. (B-C) Displacement of 125I-CCL5 (B) or 125I-CX3CL1 (C) from US28 on HEK239T membranes by monovalent or bivalent VHHs or unlabeled ligand. Monovalent VHH: open circles, bivalent VHH: filled circles and unlabeled ligand: filled squares. (D) Lack of displacement of 125I-CX3CL1 from CX3CR1-expressing HEK293T membranes by the US28 VHHs. Data shows mean±SEM. ***$P<0.001$ (unpaired t-test).
Figure 5:
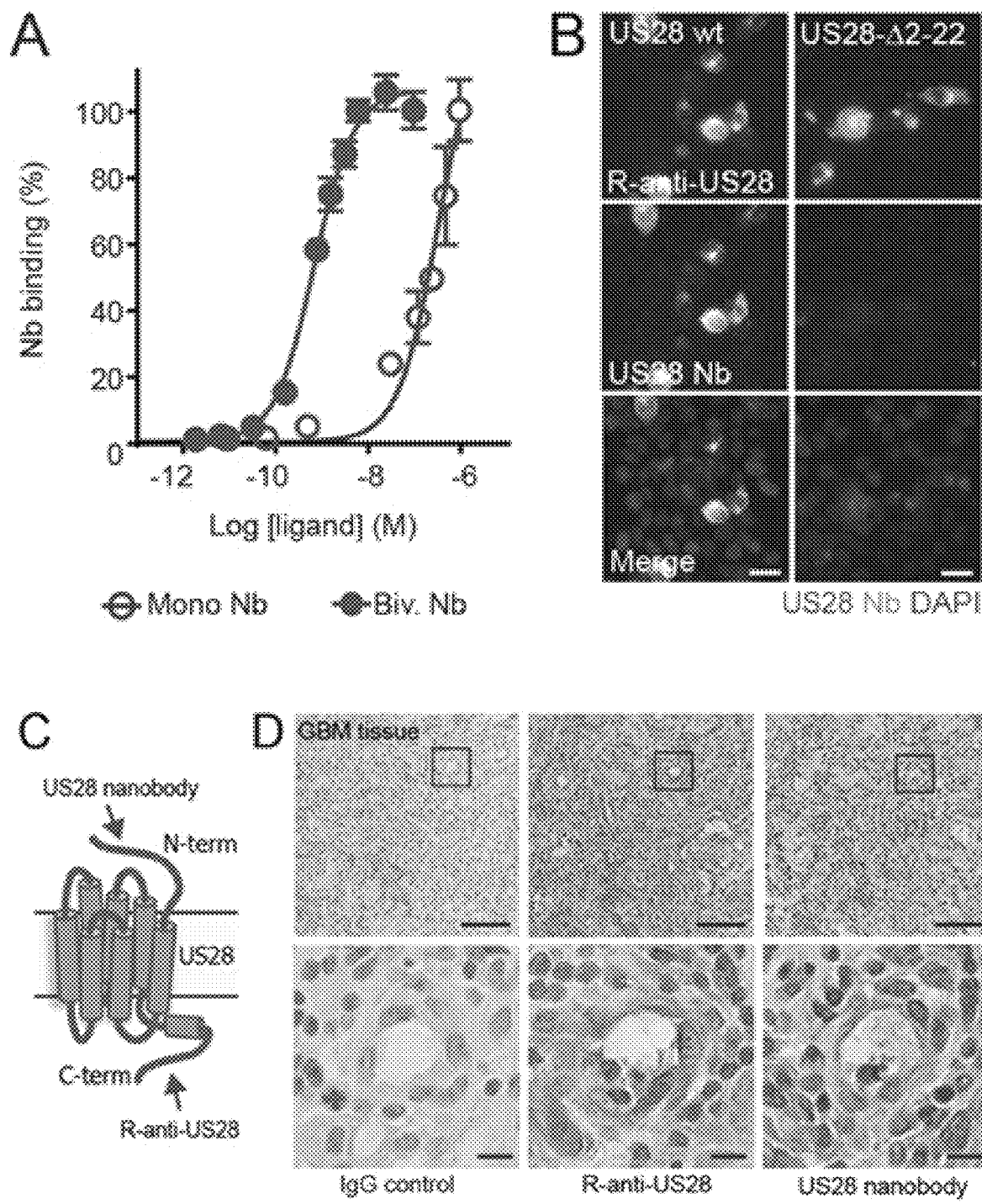
FIG. 5: VHHs bind the N-terminus of US28 and detect US28 in GBM tissue. (A) Binding of monovalent and bivalent US28-VHHs to US28-expressing HEK239T cells, as detected by flow cytometry. (B) VHH binding to US28 wild type or N-terminally truncated US28-Δ2-22 mutant, as determined by fluorescence microscopy. US28 is detected with rabbit-anti-US28 antibodies (RαUS28), VHHs with anti-Myc and nuclei with DAPI. (C) Indication of the binding epitopes of the rabbit-anti-US28 antibodies (C-terminal) and VHH (N-terminal) on US28. (D) Immunohistochemistry staining of US28 using bivalent US28-VHHs. Parallel sections of GBM patient material were stained with hematoxylin and bivalent US28 VHH or rabbit-anti-US28 antibodies. IgG isotype control (IgG) was used as control. VHHs were detected via their Myc-tag. Scale bars represent 250 µm and 100 µm (inset).

In order to study the oncomodulatory role of the HCMV-encoded chemokine receptor US28 in more detail, we set out to generate inhibitory US28-targeting VHH antibodies. Phage-display libraries were generated from RNA from peripheral blood lymphocytes of immunized llama and alpaca and this library was used in multiple rounds of phage-display selection. Output clones were screened for their ability to displace the radiolabeled chemokine CCL5 (125I-CCL5) from US28-expressing cells (FIG. 4A). One candidate that fully inhibited the binding of radiolabeled CCL5 or CX3CL1 to US28 was designated as monovalent or Mono US28-Nb (FIGS. 4B and C; Table 2). A bivalent construct of this VHH (Biv. US28-Nb) showed a 100-fold increase in affinity, when compared to a monovalent antibody, as shown in competition binding (pKi of 9.0±0.2 for CCL5 and 9.6±0.2 for CX3CL1, FIGS. 4B and C; Table 2) and flow cytometry assays (pKd of 9.2±0.1, FIG. 5A; Table 2). The anti-US28 VHH did not inhibit binding of radiolabeled CX3CL1 to its cognate human receptor CX3CR1 (FIG. 4D), illustrating its selectivity towards US28 (Gao and Murphy, 1994. JBC 269: 28539-42; Kledal et al., 1998. FEBS letters 441: 209-14). The anti-US28 VHH did not bind to a US28 mutant in which the N-terminal was truncated by deletion of 21 amino acid residues (US28-Δ2-22), indicating that its binding epitope involves the N-terminal residues of US28 (FIG. 5B). The high affinity and selectivity of the VHHs to the extracellular region of US28 (FIG. 5C) allows them to serve as a diagnostic tool for detecting US28 in patient material. To this end, bivalent VHHs were used for immunohistochemistry on parallel paraffin-embedded sections of a patient GBM tissue sample (FIG. 5D). On parallel sections, the anti-US28 VHH showed similar specific staining of US28 as a conventional US28 antibody that was raised against the C-terminus of the receptor (Slinger et al., 2010. Ibid.). Taken together, a novel US28-targeting VHH was generated which competes for chemokine binding via binding to the N-terminus of the receptor. These VHHs stained a similar US28-expressing cell population in GBM samples as the previously published polyclonal US28 antibody. These data demonstrate the potential of the US28 VHHs as a high quality US28 detection tool for ex vivo and in vivo applications.

The effect of the VHHs on US28 signaling was subsequently assessed. The CCL5-induced increase in Gaq signaling associated with an accumulation of inositol phosphates (IP) was fully inhibited by monovalent VHH (FIG. 6A) in a concentration-dependent manner (data not shown, pIC50 of 7.2±0.09 at a [CCL5] of 10-7.5 M, which equals EC80). Importantly, the bivalent VHH not only antagonized the CCL5-induced signalling, but also inhibited the constitutive US28-mediated IP accumulation in a concentration-dependent manner (α −0.52±0.02, pIC50 8.8±0.1, FIG. 6A). This inverse agonistic activity of the VHH was confirmed in an orthogonal reporter gene assay in which a bivalent VHH, but not a monovalent VHH, inhibited US28-induced NF-κB activity (α −0.50±0.08 and pIC50 8.6±0.3, FIG. 6B). In accordance with the epitope mapping data, the VHHs did not inhibit the signalling of the US28-Δ2-22 mutant (data not shown). In addition, the bivalent VHHs impaired US28-dependent foci growth and proliferation in NIH-3T3 cells (data not shown). These data demonstrate that the monovalent US28-targeting VHH acts as a competitive antagonist on US28, whereas the bivalent VHH acts both as antagonist in chemokine binding and as a partial inverse agonist in US28 signaling.

Bivalent VHH Impairs US28-Enhanced GBM Growth

Next, a bivalent US28 VHH was tested in in vitro and in vivo GBM models. In U251-iUS28 cultures, the bivalent VHH stained US28 and inhibited US28-mediated signalling and VEGF secretion (data not shown). Moreover, it significantly inhibited US28-mediated growth of U251-iUS28 spheroids by approximately 50% (FIG. 6C), which was accompanied by significantly reduced VEGF secretion (FIG. 6D). Treatment of these spheroids with the clinically approved VEGF scavenging antibody bevacizumab (BCM)/Avastin (Tijink et al., 2008. Mol Cancer Ther 7: 2288-97) reduced the US28-mediated growth of U251-iUS28 spheroids to a similar extent as the bivalent VHH (data not shown). However, BCM/Avastin did not affect 3D spheroid growth of non-induced iUS28-U251 cells, and there was no additional effect when BCM and the VHH were combined.

As a next step, the functionality of the VHH was tested in the in vivo GBM model. The blood brain barrier is a major hurdle in drug delivery in the brain. Therefore, the integrity of the tumor vasculature was first assessed by T1 weighed MRI (FIG. 6E). The observed extravasation of the contrast agent gadolinium indicates a compromised integrity of the blood brain barrier in these tumors, which prompted us to test our VHHs in this model via systemic administration. Because of their small size, VHHs display an efficient renal clearance and consequently a relatively short blood circulation time (Mujic-Delic et al., 2014. Ibid.). To enhance their circulation half-life, an additional albumin-binding VHH was added to the bivalent US28-specific VHH, creating a trivalent construct with half-life extension (designated as US28-NbHLE) (Tijink et al., 2008. Ibid.). A bivalent VHH directed against Pseudomonas transport protein PcrV (De Tavernier et al., 2016. JBC 291: 15243-55) was also half-life extended and was taken along as irrelevant control (Irr-NbHLE). US28-NbHLE displayed a similar potency/efficacy in inhibiting US28 signalling compared to the unmodified bivalent VHH, while the Irr-Nb-HLE did not show binding to US28 and did not affect US28 signalling (data not shown). Systemic intraperitoneal administration of mice bearing orthotopic U251-iUS28 tumors with US28-NbHLE significantly impaired tumor growth (FIGS. 6F and G). This inhibition was most evident on day 25 and 27 after surgery (p<0.02 and <0.04 respectively). Thus, VHHs targeting US28 and modulating its constitutive activity have therapeutic efficacy in vivo.

To determine the role of US28 signalling in GBM in a clinically more relevant context, U251 GBM cells (FIG. 7A) and GBM48 primary GBM cells (FIG. 7B) were infected with the clinically relevant HCMV Merlin strain and subsequently treated with either bivalent US28-Nb or Irr-Nb. Inhibition of US28 signalling by the bivalent US28-specific VHHs impaired the HCMV-mediated growth of both U251 spheroids and GBM48 neurospheres. From these data, it is concluded that the constitutive signalling of the viral chemokine receptor US28 plays an important role in the oncomodulatory effect of HCMV in GBM. This signalling can be inhibited by an anti-US28 VHH as described herein.

TABLE 2

Pharmacological characteristics of US28 nanobodies. Binding affinity in flow cytometry (pK$_d$), radioligand displacement (%), potency (pK$_i$ or pIC$_{50}$) and efficacy of US28 nanobodies in HEK293T cells. Mean values ± SEM are shown.

| Assay | | US28 Nb | Biv. US28 Nb |
|---|---|---|---|
| Binding affinity | pK$_d$ | 6.5 ± 0.2 | 9.2 ± 0.1 |
| $^{125}$I-CCL5 | Displ. (%) | 104 ± 10 | 119 ± 9 |
| | pK$_i$ | 7.0 ± 0.1 | 9.0 ± 0.2 |
| $^{125}$I-CX3CL1 | Displ. (%) | 77 ± 1 * | 94 ± 5 |
| | pK$_i$ | 7.2 ± 0.2 | 9.6 ± 0.2 |
| NF-$_κ$B reporter gene | Activity (a) | — | −0.50 ± 0.08 |
| | pIC$_{50}$ | — | 8.6 ± 0.3 |
| InsP accumulation | Activity (a) | — | −0.53 ± 0.02 |
| | pIC$_{50}$ | — | 8.8 ± 0.1 |

* Incomplete curve up to 10$^{-6}$M

Example 2

Materials and Methods
   As in Example 1.
Results
   Identification of Novel Anti-US28 Antibody
To find new US28-targeting antibodies, llamas were immunized with DNA encoding for US28 from the HCMV-strain VHL/e. Phage libraries with VHH genes in frame with geneIII of an M13 phagemid vector, were generated using RNA from peripheral blood mononuclear cells from these llamas. Upon 3 rounds of panning selections on US28-membrane extracts, 330 clones were screened for selective binding to US28 by means of a phage ELISA. US28-binding VHH clones were grouped in families based on the sequence of the CDR3 region. Interestingly, one of these VHH-families contained a similar, relatively short CDR3 as the previously identified US28 VHH. This new VHH was designated VUN100 (VU University Nanobody 100) and was further characterized as purified protein (FIG. 8A). As a monovalent VHH, VUN100 bound US28 with an apparent binding affinity of 2±1 nM, which is ~170 fold higher than the previously identified US28 VHHs (340±80 nM). Generation of a bivalent VUN100b protein improved the affinity by a log fold up to 0.2±0.1 nM.
   VUN100 Binds to the N-Terminus of Different US28 Strains
Because of the high similarity between the CDR3 of VUN100 and the previously selected US28 VHHs, we characterized them side-by-side in subsequent binding and ligand displacement assay. Similar to the previously published US28 VHHs, VUN100 recognized US28, but not the US28Δ2-22 mutant in which 21 amino acids from the extracellular N-terminus was removed. This indicates the importance of the N-terminus of US28 for the binding of VUN100 and suggests that this domain contributes significantly to the binding epitope of VUN100. The different US28 isoforms from different HCMV-strains only differ in a few amino acids. However, most of these variations between US28 encoded by HCMV strain VHL/e, TB40 and Merlin are found in the N-terminal domain of the receptors (FIG. 8C). Despite these variations, both the previous US28 VHHs and VUN100 were able to bind to all known US28 isoforms encoded by the different HCMV strains (FIGS. 8D and E).
   VUN100 Detects US28 in Infected GBM Patient Material
As a next step, the suitability of these VHHs to recognize US28 in paraffin-embedded GBM tissues was assessed. To that end, parallel tissue-sections from an orthotopic GBM model in the brain (striatum) in mice in which US28 expression could be induced by the administration of doxycycline (Gossen and Buiard, 1992. Proc Natl Acad Sci USA. 89: 5547-51).were used. After removing the paraffin and unmasking the epitopes, these parallel sections were stained using an antibody recognizing human nuclei, a polyclonal rabbit antibody recognizing the C-terminus of US28 or the US28 targeting VHHs (FIG. 8F). Irrelevant IgG antibodies and an irrelevant VHH were taken as negative controls. Both VHHs were able to detect US28 expression in paraffin-embedded tissue sections and the obtained staining resembled those obtained with the polyclonal US28 antibodies. Furthermore, parallel tissue-sections from HCMV-positive GBM patients were stained with the VUN100b and US28-antibody and the presence of US28 in GBM-patient material could be detected with both the antibody and VUN100b (FIG. 8G).

VUN100 Competes for Endogenous Ligand Binding and Impairs its Constitutive Activity
Next, VUN100 and VUN100b were assessed for their ability to displace the natural ligands of US28, i.e. CCL5/RANTES and CX3CL1/Fractalkine from US28 (FIGS. 9A and B, Table 2). Monovalent VUN100 and bivalent VUN100b displaced $^{125}$I-CCL5 from US28 with pKi values (M) of respectively 8.2±0.1 and 9.3±0.5. They displaced $^{125}$I-CX3CL1 with respective potencies of 8.1±0.2 and 9.4±0.4. While this means an improved potency for VUN100 over the previous monovalent US28 VHH of at least a log-fold, the new VUN100b and the previous bivalent US28 VHH appeared to be equipotent. Furthermore, both bivalent nanobodies showed similar inverse agonistic effect while no inverse agonistic effect was seen with the monovalent Nbs. That is, both nanobodies impaired the constitutive signaling of US28 towards Gaq, as determined by the US28-mediated NFAT activation (FIG. 9C) and accumulation of inositol phosphates (FIG. 9D), by approximately 50%.

In conclusion, new immunizations combined with different methods of selections and screening have yielded a new US28 targeting VHH with a superior binding affinity and potency in chemokine displacement, as compared to previously identified US28 VHH. Based on its comparable CDR3, binding epitope and ability to displace endogenous ligands, VUN100 can be regarded as an affinity-improved variant of the previously identified US28 VHH. This high binding affinity allows VUN100 to be used as targeting moiety for functional molecules (in) to US28-expressing cells.

Example 3

Material and Methods
   Immunofluorescence Microscopy
   Transiently transfected HEK293T cells were seeded in poly-L-lysine (Sigma-Aldrich) coated 96 well plates and were grown at 37° C. and 5% CO2. After 48 h, cells were fixed for 10 min at RT with 4% paraformaldehyde (PFA, Sigma-Aldrich) in PBS. Cells were washed with PBS and permeabilized for 30 min at RT with 0.5% NP-40 (Sigma-Aldrich) in PBS. Cells were washed again with PBS and wells were blocked with 1% (v/v) FBS in PBS for 1 h at RT. Nanobody (100 nM in 1% (v/v) FBS/PBS) was added to the wells and incubated for 1 h at RT. Cells were washed with PBS and afterwards incubated with Mouse-anti-Myc antibody (1:1000 in 1% (v/v) FBS/PBS, Clone 9B11, Cell Signaling). Cells were washed again with PBS and subsequently incubated with Goat-anti-Mouse-Alexa Fluor 488 (1:1000 in 1% (v/v) FBS/PBS, Thermo Fisher Scientific) for 1 h at RT. Cells were washed again with PBS and cell nuclei were stained with 4',6-diamidino-2-phenylindole (DAPI, Sigma-Aldrich) (1 µg/mL) in PBS for 10 min at RT. If US28 was visualized, cells were also incubated with the rabbit-anti-US28 antibody (1:1000, Covance (Slinger et al., 2010. Sci Signal 3: ra58)), Rat-anti-HA (1:1000, Roche) or Rabbit-anti-FLAG (1:1000, Sigma-Aldrich) for 1 h at RT. Subsequently, cells were washed and incubated with Goat-anti-Rabbit Alexa Fluor 546 (1:1000 in 1% (v/v) FBS/PBS, Thermo Fisher Scientific), Goat-anti-Rat Alexa Fluor 488 (1:1000 in 1% (v/v) FBS/PBS, Thermo Fisher Scientific) or Goat-anti-Rabbit Alexa Fluor 488 (1:1000 in 1% (v/v) FBS/PBS, Thermo Fisher Scientific). Cells were visualized with an Olympus FSX-100 microscope.
Results
   Binding of VUN100 to different US28 mutants was assessed to further determine the binding epitope of VUN100. Since the N-terminus of US28 is essential for the binding of the US28 Nb and VUN100 (Heukers et al., 2018.

Oncogene 37: 4110-4121), binding of US28 to different US28 N-terminus mutants was determined (FIG. 10A). As expected, no binding was observed of VUN100 to US28 with the cleaved N-terminus (US28 Δ2-22). Mutations of the amino acids to alanines at position 11 to 15 did not have any effect on the binding of VUN100. Interestingly, the mutation of the tyrosine at position 16 to a phenylalanine still resulted in binding of VUN100 but to a lesser extent. This suggests that the tyrosine is important for binding of VUN100 but not the only binding epitope on the N-terminus.

Since nanobodies are known to often bind discontinuous epitopes, extracellular loop (ECL)-chimaera mutants were constructed with the ECL1-3 of US28 being swapped with the corresponding ECL of the CCR5 receptor. Binding of VUN100 to these mutants was assessed by immunofluorescence microscopy (FIG. 10B). Swapping the ECL1 or ECL2 of US28 did not seem to influence binding of VUN100 to US28 indicating that these ECLs do not seem to be of importance for binding of the nanobody. The ECL3 of US28 is important for binding of VUN100 since no binding of VUN100 was observed for the US28-ECL3 chimaera.

It is thus concluded that the binding epitope of US28 Nb and VUN100 is a discontinuous epitope that is formed by the N-terminal loop (aa 1-37) and ECL3 (aa 250-273) of US28.

Example 4

Material and Methods
Reporter Gene Assay

The activation of phospholipase C was assessed as described previously ((Heukers et al., 2018. Oncogene 37: 4110-4121). Data were analyzed using GraphPad Prism version 7.0. For the NFAT-reporter gene assay, HEK293T cells were transfected with 100 ng pcDEF3-HA-US28 VHL/E and 2.5 µg NFAT reporter gene vector (Stratagene). Additional empty pcDEF3 vector was added to obtain a total amount of 5 µg DNA. Six hours post-transfection, cells were trypsinized using Trypsin-EDTA 0.05% (Gibco) and 50.000 cells were seeded per well in a Poly-L-lysine treated white bottom 96-well assay plate. Immediately after seeding, nanobodies (100 nM in DMEM) were added and incubated at 37° C. and 5% CO2. After 24 h, medium was removed and 25 µL LAR (0.83 mM D-Luciferine, 0.83 mM ATP, 0.78 µM Na2HPO4, 18.7 mM MgCl2, 38.9 mM Tris-HCl (pH 7.8), 2.6 µM DTT, 0.03% Triton X-100 and 0.39% Glycerol) was incubated for 30 min at 37° C. Luminescence (is per well) was measured using a Clariostar plate reader (BMG Labtech). Data was analyzed using GraphPad Prism version 7.0.

Results

Different bivalent VUN100-constructs with flexible GS-linkers of varying linker lengths (5-30 amino acids) or a rigid EAK linker were produced. The effect of the different bivalent VUN100 constructs on the US28 constitutive activity was determined (FIG. 11). All bivalent VUN100 nanobodies were able to inhibit the US28 constitutive activity although the inhibition of the bivalent VUN100 with a 5GS linker was somewhat less compared to the other bivalent nanobodies.

Example 5

Material and Methods
Nanobody-Photosensitizer Conjugates

The nanobody gene was re-cloned into pET28b vector to add a c-terminal cysteine (nanobody-cys) for subsequent modification. Production was performed as described previously and the nanobody was purified using chromatography (ÄKTAxpress) and 1 ml Histrap FF crude column (GE Healthcare) and 5 ml HiTrap Desalting column (GE Healthcare). The nanobody-cys was incubated with 20 mM tris(2-carboxyethyl)phosphine (TCEP) at RT for 15 min. The buffer was replaced with 50 mM sodium phosphate containing 500 mM NaCl and 1 mM EDTA using Zeba spin desalting column (Thermo Fisher Scientific). The nanobody-cys concentration was determined with the NanoDrop spectrophotometer (NanoDrop Technologies, Wilmington, Delaware, USA) at 280 nm. Immediately after buffer exchange, the nanobody-cys (1 mg/ml) was mixed with 3 molar equivalents of the photosensitizer (PS) IRDye700DX-maleimide and incubated overnight at 4° C. on a rotator. The next day, the free PS was removed by passing the solution through 3 consecutive Zeba spin desalting columns which were pre-equilibrated with 2 M NaCl in PBS. The degree of conjugation and concentration of the protein was determined using the NanoDrop by measuring the absorbance at 280 nm and 689 nm. The purity and the integrity of the nanobody-PS conjugate was determined on SDS-PAGE gel. The gel was imaged on an Odyssey Infrared scanner at 700 nm (LI-COR Biosciences).

Cell Binding Assay with Nanobody-PS

U251 cells overexpressing US28 (US28 positive) and control (US28 negative) cells were seeded at 8000 cells per well in a 96-well plate (Nunc, Roskilde, Denmark). The next day, cells were washed once with binding medium (DMEM without phenol red, 25 mM HEPES and 1% BSA, pH 7.4). Subsequently, nanobody-PS was added to the plate and incubated for 2 h at 4° C. Unbound nanobody-PS conjugate was removed by washing 3 times with binding buffer.

In Vitro PDT

The US28 positive and negative U251 cells were washed with washing medium (DMEM medium without phenol red, 10% FBS, 1% Penicillin/Streptomycin). The cells were incubated with different concentrations of nanobody-PS for 1 h at 37° C. Cells were washed 2 times with washing medium and bound and/or internalized nanobody-PS was detected using the Odyssey infrared scanner at 700 nm. Next, cells were illuminated with 5 mW/cm2 fluence rate for a total light dose of 10 J/cm2 using a 690 nm diode laser through a 600 µM optic fiber (Modulight, Tampere, Finland). After overnight incubation of the cells at 37° C., the viability of the cells was assessed by AlamarBlue® reagent, as recommended by manufacturer (Bio-Rad). Cell viability was measured with a Fluostar Optima fluorescent plate reader (BMG Labtech GmbH, Ortenberg, Germany). Cells that were neither illuminated nor treated were used to determine 100% cell viability. The percentage of cell viability was calculated relative to the untreated cells and data was analyzed using GraphPad Prism version 7.0.

In Vitro PDT in 3D Spheroids

The US28 positive and negative cells were seeded in ultra-low attachment U bottom 96 well plate (Corning). Two days after seeding, 50 µl of the medium was removed from each well and spheroids were incubated with different concentrations of nanobody-PS in washing medium for 1 hr at 37° C. After 3 times washing of the spheroids with the same medium, the plate was illuminated with 5 mW/cm2 fluence rate for a total light dose of 10 J/cm2 using a 690 nm diode laser through a 600 µM optic fiber. After overnight incubation at 37° C., the viability was assessed by CellTiter-Glo® 3D reagent as recommended by manufacturer (Promega). The percentage of cell viability was calculated relative to the untreated cells. Data was analyzed using GraphPad Prism version 7.0.

Results

Site-Directed Conjugation of IRDye700DX to VUN100

To facilitate the specific killing of US28-expressing tumor cells by PDT, the water soluble PS IRDye700DX was conjugated site-directly to VUN100. To facilitate site-directional conjugation, a VUN100 variant with an extra cysteine in its C-terminal tag (VUN100-Cys) was produced. Conjugation did not have any detrimental effect on binding specificity as VUN100-PS binds to US28 positive cells and not to negative cells (FIG. 12A).

VUN100-Targeted PDT Selectively Kills US28 Positive Cells

Next, the phototoxic effect of VUN100-PS on US28 positive and negative cells was assessed. During a pulse of 1 h at 37° C. VUN100-PS was associated specifically with the US28 positive cells, with an apparent pEC50 value of 4.3f0.8 nM which was in line with the binding affinity of VUN100 (FIG. 12B). To induce PDT, cells were exposed to a total light dose of 10 J/cm2 and cell viability was determined the following day (FIG. 12C). Phototoxicity in US28 positive cells was observed by a maximal reduction in cell viability of approximately 90% with an IC50 value of 1.1f0.2 nM. However, up to 20% cell death was also observed in the US28 negative cells at the highest concentrations of VUN100-PS. At a concentration of 10 nM of VUN100-PS, no cell toxicity was observed in the US28 negative cells, while up to 80% of the US28 positive cells were dead. This selective cell killing by VUN100-targeted PDT was validated by staining of PDT treated cells with Propidium iodide (dead cells) and Calcein (living cells, FIG. 12D). VUN100-targeted PDT induces cell toxicity in US28 expressing 3D spheroids To test whether VUN100-targeted PDT could induce similar levels of phototoxicity in a more relevant setting, we analysed their effect on 3D spheroid cultures. Two days after seeding, spheroids were incubated with VUN100-PS for 1 h at 37° C. (FIG. 12E). Already after 1 h of incubation, VUN100-PS was present in the US28 positive spheroids while no binding was seen for the US28 negative spheroids. Next, spheroids were treated with near-infrared light and cell viability was assessed the next day (FIG. 12F). In line with the results from the 2D culture experiments, VUN100-PS selectively induced cell death in up to 90% of the cells in the US28 positive spheroids while no cell death was observed in the US28 negative spheroids.

The invention claimed is:

1. A single heavy chain variable domain antibody against human cytomegalovirus protein US28 set forth in GenBank L20501, which antibody binds to the extracellular region of US28 and comprises complementarity-determining regions (CDR) with amino acid sequences F/YTGVA (SEQ ID NO:1) for CDR1; L/T/SI/T/ATG/NDGA/GTR/K (SEQ ID NO:2) for CDR2; and KTGE/RY/F (SEQ ID NO:3) for CDR3.

2. The antibody of claim 1, comprising human or humanized frame work regions.

3. The antibody of claim 1, that is fused to an immunoglobulin Fc region or functional part thereof.

4. The antibody of claim 2, wherein the Fc region or functional part thereof is human or a humanized lama Fc or functional part thereof.

5. A bi- or multivalent antibody comprising the single heavy chain variable domain antibody according to claim 1.

6. A bi- or multispecific antibody comprising a heavy chain variable domain antibody of claim 1.

7. The bi- or multispecific antibody according to claim 6, further comprising a single heavy chain variable domain antibody against a serum protein.

8. The antibody according to claim 1, which is coupled to a detectable label.

9. The antibody according to claim 1, which is coupled to a cytotoxic drug.

10. A pharmaceutical composition comprising an antibody of claim 1.

11. The single heavy chain variable domain antibody against human cytomegalovirus protein US28 of claim 1, which antibody binds to N-terminal extracellular region of US28.

12. The antibody of any one of claim 1, that is fused to an immunoglobulin Fc region or functional part thereof that is from, or derived from, IgG1, IgG2, IgG3, or IgG4.

13. The antibody according to claim 1, which is coupled to a fluorescent label, a luminescent label, a (radio)isotope label or a paramagnetic label.

14. The antibody according to claim 1, comprising complementarity-determining regions (CDR) with amino acid sequences FTGVA (SEQ ID NO:1) for CDR1; LITGDGATR (SEQ ID NO:2) for CDR2; and KTGEY (SEQ ID NO:3) for CDR3.

15. The antibody according to claim 1, wherein the antibody comprises the sequence (SEQ ID NO: 11)
EVQLVESGGGLVQPGGSLRLACAVSGPGLIFKFTGVAWYRRQVPGAKRGLV

ALITGDGATRYGDSVKGRFTVSRDIAAKRVYLEMNDLRSEDTAVYYCKTGE

YWGQGTQVTVSS.

16. The antibody according to claim 1, comprising complementarity-determining regions (CDR) with amino acid sequences YTGVA (SEQ ID NO:1) for CDR1; TTTNDGGTK (SEQ ID NO:2) for CDR2; and KTGRF (SEQ ID NO:3) for CDR3.

17. The antibody according to claim 1, wherein the antibody comprises the sequence (SEQ ID NO: 12)
EVQLVESGGGLVQAGGSLRLSCVVSGTIFSYTGVAWYRQTSGKQREWVATT

TNDGGTKFADSVKGRFTISRDNAKKTVYLQMNNLNAEDTAVYYCKTGRFWG

RGTLVTVSS.

18. The antibody according to claim 1, comprising complementarity-determining regions (CDR) with amino acid sequences YTGVA (SEQ ID NO:1) for CDR1; TATNDGGTK (SEQ ID NO:2) for CDR2; and KTGRF (SEQ ID NO:3) for CDR3.

19. The antibody according to claim 1, wherein the antibody comprises the sequence (SEQ ID NO: 13)
EVQLVESGGGLVQAGGSLRLSCVVSGTIFSYTGVAWYRQTSGNQREWVATA

TNDGGTKFADSMKGRFTISRDNAKKTVYLQMNNLNAEDAAVYYCKTGRFWG

RGTLVTVSS.

20. The antibody according to claim 1, comprising complementarity-determining regions (CDR) with amino acid sequences YTGVA (SEQ ID NO:1) for CDR1; SATNDGGTK (SEQ ID NO:2) for CDR2; and KTGRF (SEQ ID NO:3) for CDR3.

21. The antibody according to claim 1, wherein the antibody comprises the sequence

```
                                    (SEQ ID NO: 14)
EVQLVESGGGLVQAGGSLRLSCVVSGTIFSYTGVAWYRQTSGNQREWVASA

TNDGGTKFADSVKGRFTISRDNAKKTVHLQMNNLNAEDAAVYYCKTGRFWG

RGTLVTVSS.
```

22. The antibody according to claim 1, wherein the antibody comprises the sequence

```
                                    (SEQ ID NO: 15)
EVQLVESGGGLVQAGGSLRLSCVVSGTIFSYTGVAWYRQPSGKQREWVASA

TNDGGTKFADSVKGRFTISRDNAKKTVYLQMNNLDADDTAVYYCKTGRFWG

RGTLVTVSS.
```

* * * * *

UNITED STATES PATENT AND TRADEMARK OFFICE
CERTIFICATE OF CORRECTION

PATENT NO. : 12,037,382 B2
APPLICATION NO. : 16/967269
DATED : July 16, 2024
INVENTOR(S) : Martine Joyce Smit et al.

It is certified that error appears in the above-identified patent and that said Letters Patent is hereby corrected as shown below:

On the Title Page

Item (72) Inventors; Line 1:
Delete "Amsterdan" and insert --Amsterdam--

Signed and Sealed this
Twenty-seventh Day of August, 2024

Katherine Kelly Vidal
*Director of the United States Patent and Trademark Office*